United States Patent [19]

Yamamoto

[11] Patent Number: 5,053,333

[45] Date of Patent: Oct. 1, 1991

[54] PROTEASE

[75] Inventor: Hiroaki Yamamoto, Hyogo, Japan

[73] Assignee: M & D Research Co., Ltd., Tokyo, Japan

[21] Appl. No.: 301,988

[22] Filed: Jan. 26, 1989

[30] Foreign Application Priority Data

Jan. 27, 1988 [JP] Japan .................................. 63-16285
Aug. 12, 1988 [JP] Japan ............................... 63-201285

[51] Int. Cl.$^5$ .............................................. C12N 9/48
[52] U.S. Cl. ..................................... 435/212; 435/219; 435/224
[58] Field of Search ........................ 435/212, 219, 224

Primary Examiner—Lester L. Lee
Assistant Examiner—Eric J. Kraus
Attorney, Agent, or Firm—Birch, Stewart, Kolasch & Birch

[57] ABSTRACT

There is disclosed a protease having the following enzymatic properties in view of:
(a) function and substrate specificity,
(b) optimum pH,
(f) activation, and
(g) inhibition;

(a) the protease can hydrolyze, in particular, a peptide bond on the C-terminal side of Y of a peptide X—Y—, in which X is Arg, Lys or Pro optionally having a peptide bond on the N-terminal side, Y is Arg and — indicates a peptide bond;

(b) the protease has an optimum pH of about 7.0 in Tris hydrochloride buffer;

(f) the protease is activated with calcium chloride or a surfactant; and (g) the protease is inhibited with p-amidinophenylmethanesulfonyl fluoride, p-chloromercuribenzoic acid, a metal chelater, tetraacetic acid or a heavy metal.

36 Claims, 13 Drawing Sheets

Fraction No.

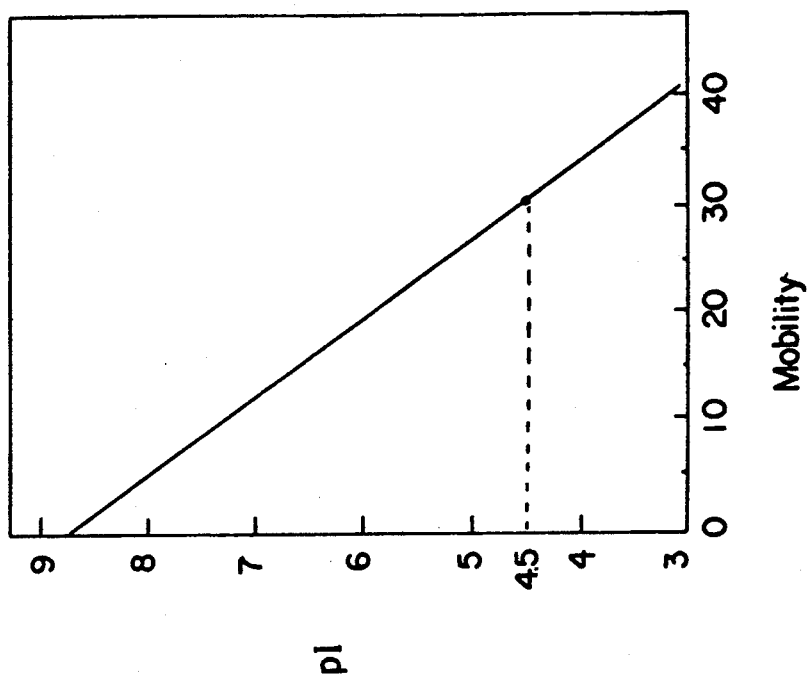

PROTEASE

This invention relates to a novel protease. More particularly, it relates to a protease specific for paired basic amino acid residues.

PRIOR ART

It has been suggested that a protease specific for paired basic amino acid residues participates in the synthesis of a hormone from the corresponding prohormone. Thus it has been attempted to purify these proteases from various sources in order to clarify the enzymatic properties and physiological functions and to thereby apply the high specificity thereof to the synthesis of a hormone from a prohormone or to the limited proteolysis of proteins or peptides. Among these proteases, those which have been completely purified hitheroto are limited to the following ones: IRCM-serine protease-1 originating from swine pituitary (cf. J. Biol. Chem., 261, 10850 (1986)); POMC-converting enzyme originating from bovine pituitary (cf. J. Biol. Chem., 260, 7194 (1985) and ibid., 261, 14392 (1986)), phorcesin Y-1 originating from a yeast (*Saccharomyces cerevisiae*) (cf. Nature, 309, 558 (1984)).

The IRCM-serine protease-1 and the phorcesin Y-1 are classified as serine proteases while the POMC-converting enzyme is classified as aspartic protease. The protease specific for paired basic amino acid residues originating from Sporobolomyces and Kluyveromyces is inhibited by p-amidinophenylmethanesulfonyl fluoride (pAPMSF), p-chloromercuribenzoic acid (pCMB), metal chelaters and heavy metals. It is known that the IRCM-serine protease-1, the POMC-converting enzyme and the protease specific for paired basic amino acid residues originating from Sporobolomyces and Kluyveromyces would specifically hydrolyze at the C-terminal side of paired basic amino acids while the phorcesin Y-1 would specifically hydrolyze between paired basic amino acids. In addition, a protease specific for paired basic amino acid residues, which is presumed to be KEX2-protease participating in the processing of the α-mating factor, has been partially purified from a yeast *Saccharomyces cerevisiae* (cf. Biochem. Biophys. Res. Commun., 144, 807 (1987)). Further the cloning of KEX2-protease has been reported (cf. Biochem. Biophys. Res. Commun. 156, 246–254 (1988)).

However none of proteases reported so far is satisfactory in, for example, enzyme activity and stability.

When a protease is to be applied to the synthesis of hormones from prohormones or fusion proteins synthesized by recombinant technology, it is preferable that said protease specifically cleaves at the C-terminal side of consecutive basic amino acid residues. Thus it is expected to detect such a protease.

SUMMARY OF THE INVENTION

The invention provides a protease having the following physico-chemical properties in view of:
(a) function and substrate specificity,
(b) optimum pH,
(f) activation,
(g) inhibition,
(a) the protease can hydrolyze, in particular, a peptide bond on the C-terminal side of Y of a peptide X—Y—, in which X is Arg, Lys or Pro optionally having a peptide bond on the N-terminal side, Y is Arg and — indicates a peptide bond;
(b) the protease has an optimum pH of about 7.0 in Tris-hydrochloride buffer;
(f) it is activated with calcium chloride or a surfactant; and
(g) it is inhibited with p-amidinophenylmethanesulfonyl fluoride, p-chloromercuribenzoic acid, a metal chelater, tetraacetic acid or a heavy metal.

The protease of the invention can be preferably obtained from a culture broth in which a yeast belonging to the genus Sporobolomyces, Kluyveromyces, Filobasidium, Hansenula, Issatchenkia, Pichia, Rhodosporidium or Saccharomycopsis has been cultured.

The protease defined above according to the invention includes embodiments A and B.

The proteases A and B have common properties with respect to properties (a) and (b), but have properties different from each other with respect to properties (c), (d) and (e) as follows:
(c) pH stability
(d) optimum temperature and
(e) heat stability;
(c) protease A is most stable at pH 6.0 to 8.0 protease B and at pH 6.0 to 10
(d) optimum temperature for protease A is about 40 to 47 degrees C. at pH 7.0 and about 60 degrees C. at pH 7.0 for protease B; and
(e) protease A is stable to 38 degrees C. at pH 7.0 for 10 minutes and protease B stable to 55 degrees C. at pH·7.0 for 10 minutes.

The invention also provides another protease A' which has been obtained from a culture broth in which a yeast belonging to the genus Sporobolomyces has been cultured and is not restricted with regard to the properties (b) to (e).

The invention also provides a protease B' which has been obtained from a culture broth in which a yeast belonging to the genus Kluyveromyces, Filobasidium, Hansenula, Issatchenkia, Pichia, Rhodosporidium or Saccharomycopsis has been cultured and is not restricted with regard to the properties (b) to (e).

The invention will be shown below in reference to the embodiments thereof, i.e. A, A', B and B'.

Protease B and B'

Under these circumstances, the present inventors have attempted to detect a protease satisfying the above requirements from yeasts available in a large amount. As a result, the present inventors have found that a protease satisfying the above requirements can be produced by a yeast belonging to the genus Kluyveromyces, Filobasidium, Hansenula, Issatchenkia, Pichia, Rhodosporidium or Saccharomycopsis, succeeded in the purification of said enzyme and clarified the physicochemical properties of the same, thus completing the present invention.

Accordingly, the present invention provides a protease having the following physicochemical properties (a) to (e):
(a) function and substrate specificity: can hydrolyze, in particular, a peptide bond at the C-terminal side of Y of a peptide X—Y—, wherein X is Arg, Lys or Pro optionally having a peptide bond on the N-terminal side; Y is Arg and — represents a peptide bond;
(b) optimum pH: around 7.0 in Tris-hydrochloride buffer solution;
(c) pH stability: most stable at 6 to 10;
(d) optimum temperature: around 60° C (pH 7.0); and (e) heat stability: stable at 55° C or below (at pH 7.0 for 10 minutes).

The physicochemical properties of the protease of the present invention, other than the abovementioned ones, and the enzymological properties thereof are as follows:

(f) activation: activated by calcium chloride and surfactants such as Lubrol PX or Triton X-100;

(g) inhibition: inhibited by, for example, p-amidinophenylmethanesulfonyl fluoride (pAPMSF), p-chloromercuribenzoic acid (pCMB), metal chelaters such as ethylenediaminetetraacetic acid (EDTA) or ethylene glycol bis(2-aminoethyl ether) tetraacetic acid (EGTA) and heavy metals such as copper(II)sulfate, zinc chloride or mercury (II) chloride; and (h) molecular weight: approximately 100,000 when determined by gel filtration with the use of TSK gel G3000 $SW_{XL}$.

In the present invention, the activity of the protease is determined in the following manner.

Determination of activity:

1 ml of a reaction mixture containing 50 μmol of Tris-hydrochloride buffer (pH 7.0), 10 mg of Lubrol PX, 0.5 μmol of calcium chloride, 0.1 μmol of Boc-Gln-Arg-Arg-MCA, wherein Boc represents a t-butyloxycarbonyl group while MCA represents 4-methylcoumarin-7-amide and the enzyme is allowed to react at 30° C. The fluorescence (excition wavelength: 380 nm, emmision wavelength: 460 nm) originating from the 7-amino-4-methylcoumarin (AMC) thus formed is monitored with the lapse of time. The amount of the enzyme activity capable of catalyzing the release of 1 n mol of AMC per one minute is defined as 1 U. The specific activity is represented by U per mg of protein. The amount of the protein is determined by measurement the absorbance at 280 n mol as $E^{1\%}$ of protein being assumed to be 10.

In the present invention, the microorganisms capable of producing a protease specific for paired basic amino acid residues include all strains, mutants and variants capable of producing a protease specific for paired basic amino acid residues belonging to the genera Kluyveromyces, Filobasidium, Hansenula, Issatchenkia, Pichia, Rhodosporidium and Saccharomycopsis. Among these strains, the following ones are preferable: *Kluyveromyces lactis* IFO 1903 and IFO 1267; *Filobasidium capsuligenum* IFO 1119 and IFO 1185; *Hansenula fabianii* IFO 1253 and IFO 1254; *Hansenula holstii* IFO 0980 and IFO 0986; *Hansenula polymorpha* ATTC 26012; *Issatchenkia scutulata* var. scutulata IFO 10069 and IFO 10070; *Pichia heedii* IFO 10019, 10020; *Pichia heedii* var. thermotolerans IFO 10024, IFO 10025 and IFO 10026; *Rhodosporidium diovovatum* IFO 1830; *Rhodosporidium toruloides* IFO 0413 and IFO 0080; and *Saccharomycopsis fibuligera* IFO 0103, IFO 0105 and IFO 0106.

The above shown strains are available to public at Institute for Fermentation, Osaka, of 17-85, Juso-Honmachi 2 chome, Yodogawa-ku, Osaka 532, Japan. These strains were open to public before the filing of the present application.

The protease specific for paired basic amino acid residues of the present invention may be prepared by culturing a strain capable of producing said protease and belonging to one of the genera as defined above in a common medium such as a YM medium and purifying the aimed protease specific for paired basic amino acid residues from the culture broth. It is not required to add any particular inducer to the medium. It is preferable to carry out the culture at 25° to 37° C. for one to three days. The protease specific for paired basic amino acid residue thus produced may be purified by combining conventional techniques. For example, the culture medium is centrifuged to thereby collect the cells which are then disrupted with, for example, a Dyno-Mill(-trademark). Then the homogenate is centrifuged to thereby separate pellets including residual cells and the supernatant is ultracentrifuged at, for example, 150,000 g for 60 minutes to thereby give a membrane fraction. The desired enzyme is solubilized from the membrane fraction with the use of a surfactant and then purified by, for example, a heat treatment, ion exchange chromatography, affinity chromatography and gel filtration.

Protease A and A'

These are produced preferably with a yeast belonging to the genus Sporobolomyces, and have the following enzymatic properties (a) to (e).

(a) function and substrate specificity: can hydrolyze, in particular, a peptide bond at the C-terminal side of Y of a compound X—Y—, wherein X is Arg, Lys or Pro optionally having a peptide bond on the N-terminal side, Y is Arg and — represents a peptide bond;

(b) optimum pH: around 7.0 in Tris-hydrochloride buffer;

(c) pH stability: the most stable at 6.0 to 8.0 (showing a residual activity of 80% or above after being treated at pH 6 to 8 at 30° C. for 30 minutes);

(d) optimum temperature: around 40° to 47° C. (pH 7.0) and (e) heat stability: stable at 38° C. or below (showing no decrease in activity when heated at pH 7.0 for 10 minutes).

The enzymatic properties of the protease of the present invention, other than the abovementioned ones, and the enzymatic properties thereof are as follows:

(f) activation: It is best activated with use of calcium chloride having a low concentration. It can be also activated by a surfactant such as Lubrol PX and Triton X-100.

(g) inhibition: inhibited by metal chelaters such as ethylenediaminetetraacetic acid (EDTA) or ethylene glycol bis(2-aminoethyl ether)tetraacetic acid (EGTA) or heavy metal compounds such as copper(II) sulfate, zinc chloride or mercury(II) chloride. Also inhibited by p-chloromercuribenzoic acid (p-CMB) or p-amidinophenylmethanesulfonyl chloride (p-APMSF).

(h) molecular weight: approximately 47,000 as determined by gel filtration with the use of TSK gel G3000 $SW_{XL}$.

(i) isoelectric point: 4.5 as determined by isoelectric electrophoresis.

In the present invention, the activity of the protease is determined in the following manner.

Determination of activity:

A reaction mixture containing 50 μmol of tris hydrochloride buffer solution (pH 7.0), 10 mg of Lubrol PX, 0.5 μmol of calcium chloride, 0.1 μmol of Boc-Gln-Arg-Arg-MCA, wherein Boc represents a t-butyloxycalbonyl group while MCA represents 4-methylcoumarin-7-amide and the enzyme is allowed to react at 30° C. The fluorescence (excition wavelength: 380 nm, emission wavelength: 460 nm) originating from the 7-amino-4-methylcoumarin (AMC) thus formed is monitored. The amount of the enzyme capable of catalyzing the release of 1 nmol of AMC per one minute is defined as 1 U.

In the present invention, the microorganisms capable of producing a protease specific for a basic amino acid residue include all strains, mutants and variants capable of producing a protease specific for paired basic amino acid residue belonging to the genus Sporobolomyces. Among these strains, *Sporobolomyces odrus* IFO 1597 is preferable.

The protease specific for paired basic amino acid residue of the present invention may be prepared by, for example, culturing a strain capable of producing said protease and belonging to the genus Sporobolomyces in a common medium such as a YM medium and purifying the aimed protease specific for a paired basic amino acid residues from the culture medium. It is not necessary to add any particular inducer to the medium. It is preferable to carry out the culture at 25° to 37° C. for one to three days.

The protease specific for a basic amino acid residue thus produced may be purified by combining conventional techniques. For example, the culture medium is centrifuged to thereby collect the cells, which are then disrupted with, for example, a Dyno-Mill (trademark). Then the homogenate is centrifuged at a low rate to thereby separate pellets including residual cells and the supernatant is ultracentrifuged at, for example, 150,000 g for 60 minutes to thereby give a membrane fraction. The desired enzyme is solubilized from the membrane fraction with the use of a surfactant and then purified by, for example, ammonium sulfate fractionation, a heat treatment, ion exchange chromatography, affinity chromatography and gel filtration.

BRIEF DESCRIPTION OF THE DRAWINGS

FIG. 26 shows the results of the isoelectric electrophoresis of the protease specific for a basic amino acid residue of the present invention with the use of IEF gel 3 - 9.

EXAMPLES

Figure 1:
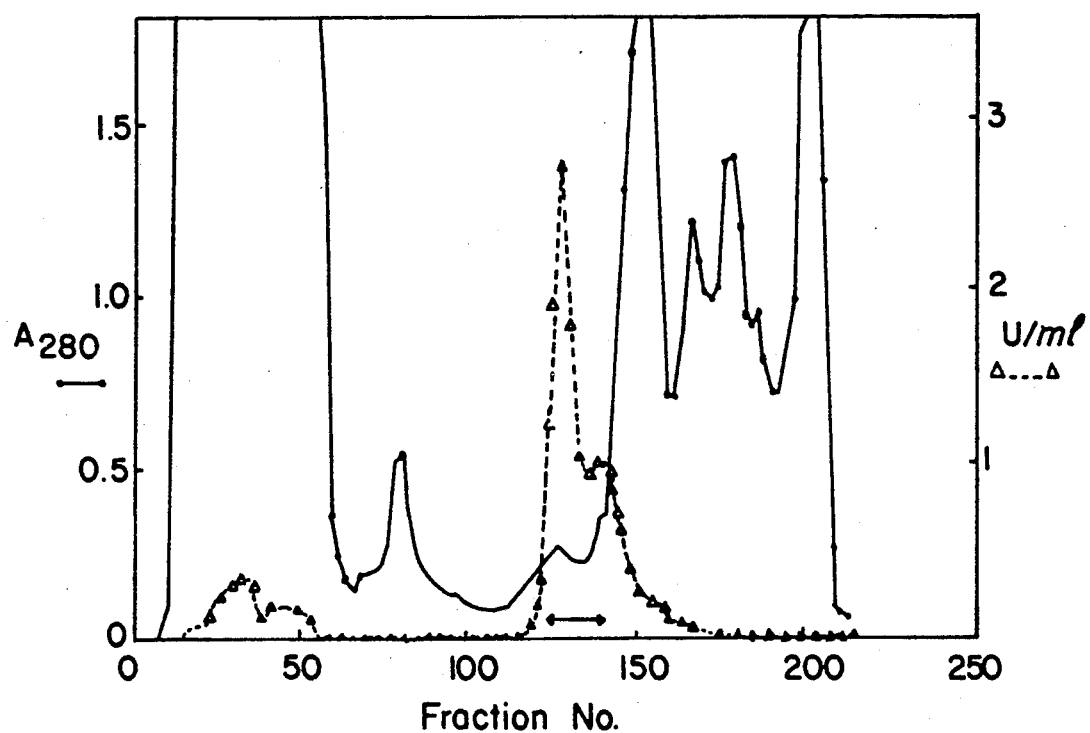
FIG. 1 is a DEAE/Toyopearl chromatogram formed in the purification of a protease specific for a basic amino acid residue from *Kluyveromyces lactis* IFO 1903.

To further illustrate the present invention, and not by way of limitation, the following Examples will be given.

EXAMPLE 1

Screening of protease specific for basic amino acid residue

Various yeasts were cultured each in 750 l of a YM medium (pH 6.0) containing 10 g/l of glucose, 5 g/l of bactopeptone, 3 g/l of yeast extract and 3 g/l of malt extract for two days. The culture medium was centrifuged at 6,700 g for ten minutes to thereby give moist cells These moist cells were ground in alumina and then further ground ultrasonically for one minute The ground cells were centrifuged at 1,000 g for ten minutes and the supernatant thus obtained was further ultracentrifuged at 80,000 g for 30 minutes. Thus a membrane fraction was prepared as the precipitate.

The obtained membrane fraction was suspended in an extraction buffer solution (10 mM tris hydrochloride buffer solution, pH 7.0, containing 1% of Lubrol PX and 0.1M of sodium chloride) and stirred at 4° C. for one hour to thereby solubilize the membrane protein The suspension was ultracentrifuged at 80,000 g for 30 minutes and the activity of the protease specific for a basic amino acid residue in the membrane extract, namely, the supernatant thus obtained was determined.

Further the membrane extract was heated to 50° C. for ten minutes and centrifuged at 15,000 g for 30 minutes. The activity of the protease specific for a basic amino acid residue in the supernatant thus obtained, which was referred to as a heat-treated membrane extract, was determined.

Table 1 summarizes the results.

TABLE 1

Screening of protease specific for basic amino acid residue

| Strain | | Moist wt. (g) | Specific activity (U/ml) | |
|---|---|---|---|---|
| | | | membrane extract | heat-treated membrane extract |
| *Kluyveromyces lactis* | IFO 1903 | 6.06 | 0.0993 | 0.280 |
| *Kluyveromyces lactis* | IFO 1267 | 6.56 | 0.0288 | 0.164 |
| *Filobasidium capsuligenum* | IFO 1119 | 10.6 | 0.257 | 0.0828 |
| *Filobasidium capsuligenum* | IFO 1185 | 8.03 | 0.0318 | 0.00485 |
| *Hansenula fabianii* | IFO 1253 | 4.63 | 0.0720 | 0.0330 |
| *Hansenula fabianii* | IFO 1254 | 6.11 | 0.0988 | 0.101 |
| Hansenula | IFO 0980 | 6.90 | 0.457 | 0.242 |
| Hansenula | IFO 0986 | 6.10 | 0.146 | 0.125 |
| *Hansenula polymorpha* | ATCC 26012 | 4.99 | 0.150 | 0.176 |
| Issatchenkia var. | IFO 10069 | 7.93 | 0.0177 | 0.0243 |
| Issatchenkia var. | IFO 10070 | 9.28 | 0.0365 | 0.0290 |
| Pichia | IFO 10019 | 4.40 | 0.132 | 0.136 |
| Pichia | IFO 10020 | 4.98 | 0.188 | 0.197 |
| *Pichia via. thermotolerans* | IFO 10024 | 1.27 | 0.248 | 0.192 |
| *Pichia via. thermotolerans* | IFO 10025 | 3.88 | 0.252 | 0.170 |
| *Pichia via. thermotolerans* | IFO 10026 | 1.42 | 0.151 | 0.188 |
| Rhodosporidium | IFO 1830 | 5.69 | 0.0101 | 0.0107 |
| Rhodosporidium | IFO 0413 | 5.56 | 0.342 | 0.198 |
| Rhodosporidium | IFO 0880 | 5.10 | 0.132 | 0.0427 |
| *Saccharomycopsis fibuligera* | IFO 0103 | 12.3 | 0.106 | 0.139 |
| *Saccharomycopsis fibuligera* | IFO 0105 | 13.5 | 0.0353 | 0.0358 |
| *Saccharomycopsis fibuligera* | IFO 0106 | 6.22 | 0.0655 | 0.0598 |

EXAMPLE 2

Purification of protease specific for basic amino acid residue from *Kluyveromyces lactis* IFO 1903

*Kluyveromyces lactis* IFO 1903 was cultured in 30 l of a YM medium for two days The culture medium was centrifuged to thereby give 314 g (moist weight) of cells. These cells were suspended in 300 ml of a buffer solution 1 (10 mM tris hydrochloride buffer solution, pH 7.0, containing 0.5 mM of calcium chloride) and ground with a mill. Then the mixture was centrifuged at 1,700 g for ten minutes to thereby remove residual cells. The obtained supernatant was ultracentrifuged at 150,000 g for 60 minutes. Thus 79.4 g of a membrane fraction was obtained as the precipitate. The membrane fraction was suspended in an extraction buffer solution (10 mM tris hydrochloride buffer solution, pH 7.0, containing 3% of Lubrol PX and 0.1 M of sodium chloride) and stirred overnight to thereby extract the enzyme. After ultracentrifuging under the same conditions as those described above, a membrane extract was obtained as the supernatant.

The membrane extract was heated to 50° C. for 30 minutes and the precipitate thus formed was removed by centrifuging at 39,000 g for 20 minutes. The supernatant was concentrated by ultrafiltration and then dialyzed against a buffer solution 2 (10 mM tris hydrochloride buffer solution, pH 7.0, containing 0.5 mM of calcium chloride and 0.2% of Lubrol PX). The fraction thus obtained was referred to as the heat-treated membrane extract.

This fraction was poured into a DEAE/Toyopearl 650M column (2.5×40 cm) which had been preliminarily equilibrated with the buffer solution 2. After thoroughly washing the column with said buffer solution, the enzyme was eluted by gradient elution with 0 to 0.6M sodium chloride to thereby give an active fraction. FIG. 1 shows the elution pattern.

Figure 2:
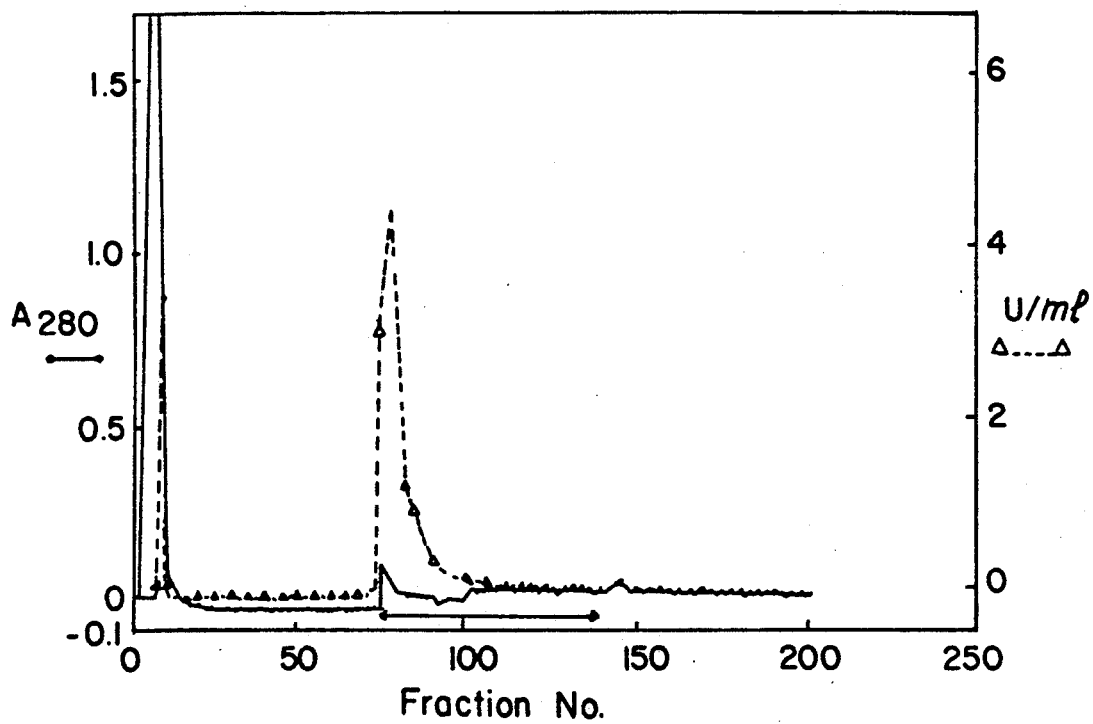
FIG. 2 is a Con A/Sepharose chromatogram formed in the purification of a protease specific for a basic amino acid residue from *Kluyveromyces lactis* IFO 1903.

The active fraction was concentrated by ultrafiltration and poured into a concanavalin A (Con A)/Sepharose column (1.6×25 cm) which had been preliminarily equilibrated with the buffer solution 2 containing 0.5M of sodium chloride. After thoroughly washing the column with said buffer solution, the enzyme was eluted with the buffer solution 2 containing 0.5M of sodium chloride and 0.67M of α-methyl-D-mannoside. FIG. 2 shows the elution pattern. The active fraction was concentrated and referred to as the Con A/Sepharose fraction.

Figure 3:
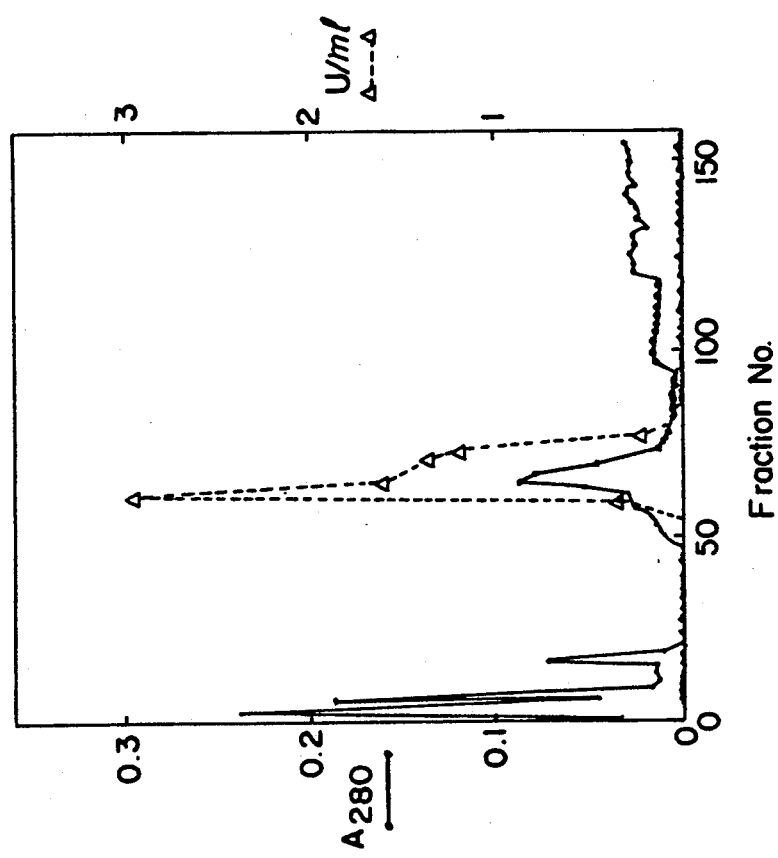
FIG. 3 is an arginine/Sepharose chromatogram formed in the purification of a protease specific for a basic amino acid residue from *Kluyveromyces lactis* IFO 1903.

The Con A/Sepharose fraction was dialyzed against the buffer solution 2 and poured into an arginine/Sepharose column (1.6×50 cm) which had been preliminarily equilibrated with said buffer solution. After thoroughly washing the column, the enzyme was eluted by gradient elution with 0 to 0.5M of sodium chloride. FIG. 3 shows the elution pattern. The active fraction was concentrated by ultrafiltration and referred to as the arginine/Sepharose fraction.

Figure 4:
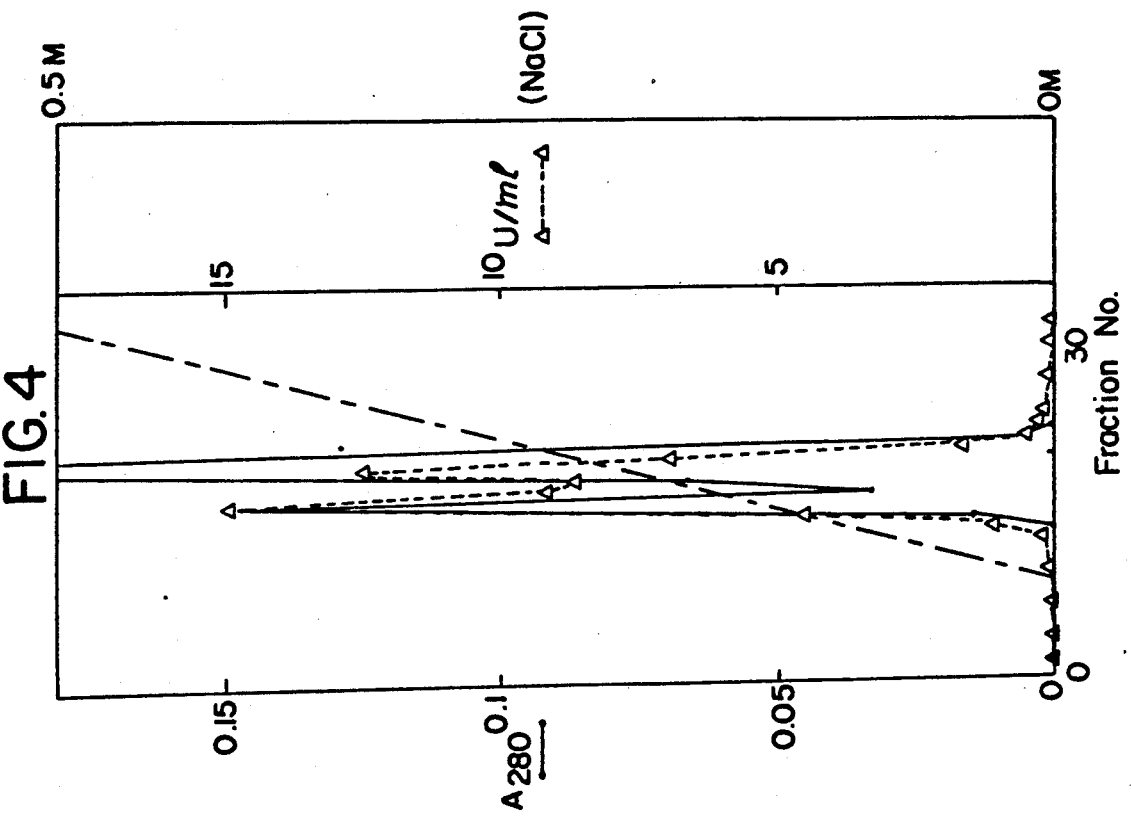
FIG. 4 is a Mono Q chromatogram formed in the purification of a protease specific for a basic amino acid residue from *Kluyveromyces lactis* IFO 1903.

The arginine/Sepharose fraction was dialyzed against the buffer solution 2 and then poured into a Mono Q column (0.5×5.0 cm) which had been preliminarily equilibrated with said buffer solution. After washing thoroughly the column with said buffer solution, the enzyme was eluted by gradient elution with 0 to 0.5M of sodium chloride. FIG. 4 shows the elution pattern. Thus two peaks were obtained each as an active fraction. These peaks were collected separately and concentrated. They were referred to as the Mono Q-I and Q-II fractions, respectively.

Figure 6:
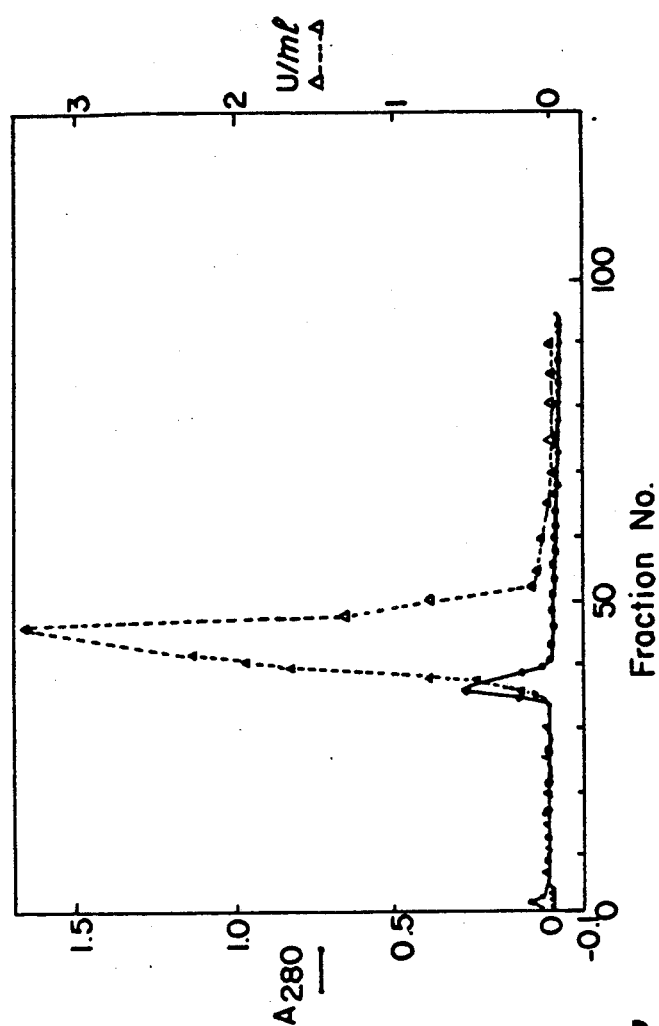
FIG. 6 is a benzamidine/Sepharose chromatogram of Mono Q-II formed in the purification of a protease specific for a basic amino acid residue from *Kluyveromyces lactis* IFO 1903.
Figure 5:
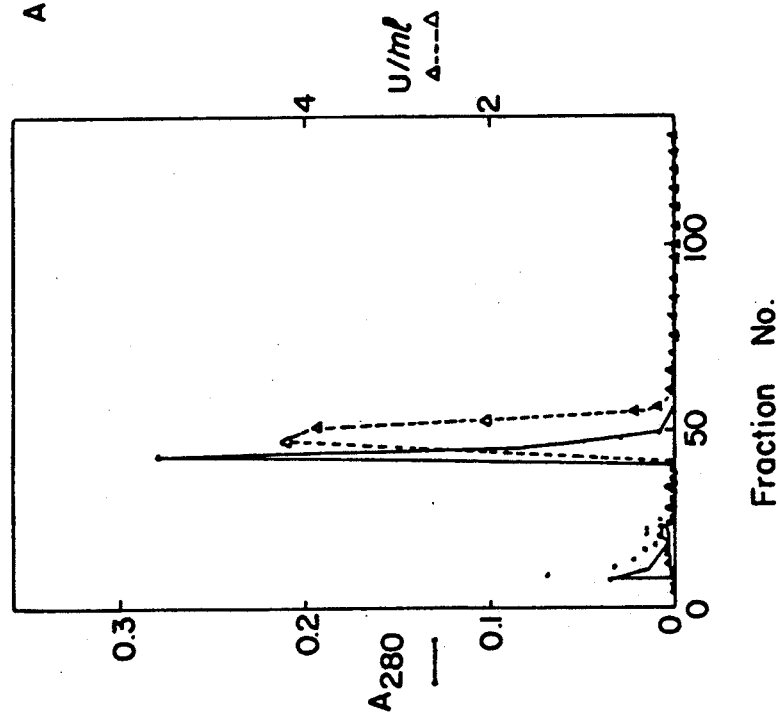
FIG. 5 is a benzamidine/Sepharose chromatogram of Mono Q-1 formed in the purification of a protease specific for a basic amino acid residue from *Kluyveromyces lactis* IFO 1903.

These fractions were separately dialyzed against the buffer solution 2 and each poured into a benzamidine/Sepharose column (1.6×5.0 cm) which had been preliminarily equilibrated with said buffer solution. After thoroughly washing the column with said buffer solution, the enzyme was eluted by gradient elution with 0 to 0.5M of sodium chloride. FIGS. 5 and 6 show the elution patterns corresponding to the Mono Q-I and Mono Q-II, respectively. The active fractions thus obtained were referred to as Benz-I and Benz-II, respectively, Table 2 summarizes the results.

TABLE 2

Purification of protease specific for basic amino acid residue from *Kluyveromyces lactis* IFO 1903

| Step | Volume (ml) | Protein (mg) | Activity (U) | Specific activity (U/mg) | Yield (%) | Purification ratio |
|---|---|---|---|---|---|---|
| membrane extraction | 1,450 | 15,000 | 52.4 | 0.00350 | | 1 |
| heat treatment | 537 | 11,000 | 989 | 0.0896 | 100 | 26 |
| DEAE/Toyopearl | 20.7 | 467 | 800 | 1.71 | 81 | 489 |
| Con A/Sepharose | 33.0 | 24.3 | 657 | 27.0 | 66 | 7,730 |
| arginine/Sepharose | 17.1 | 12.8 | 326 | 25.4 | 33 | 7,260 |
| Mono Q-I | 1.5 | 1.52 | 84.5 | 55.5 | 8.5 | 15,900 |
| Benz-I | 0.42 | 0.377 | 37.3 | 98.8 | 3.8 | 28,200 |
| Mono Q-II | 2.1 | 2.90 | 73.6 | 25.4 | 7.4 | 7,260 |
| Benz-II | 0.55 | 0.431 | 25.2 | 58.4 | 2.5 | 16,700 |

Benz-I may be presumed to be a decomposition product of Benz-II from the reactions of them with inhibitors, the fact that the optimum pH values thereof are nearly the same with each other and the molecular weights thereof (Benz-I: approximately 60,000 to 100,000, Benz-II: approximately 100,000), as will be shown hereinafter.

As shown in Table 2, the relative activity of Benz-I is higher than that of Benz-II. Thus the following description, which will sometimes exclusively relate to Benz-I, will be also applied to Benz-II.

EXAMPLE 3

Substrate specificity of protease specific for basic amino acid residue originating from *Kluyveromyces lactis* IFO 1903.

The activities of Benz-I and Benz-II were determined under standard conditions with the use of various fluorescent substrates. The activity for each substrate was expressed by relative activity with the activity for Boc-Gln-Arg-Arg-MCA being 100. Table 3 shows the results.

TABLE 3

Substrate specificity of protease specific for basic amino acid residue originating from *Kluyveromyces lactis* IFO 1903

| Substrate | Benz-I | Benz-II |
|---|---|---|
| Boc—Gln—Arg—Arg—MCA | 100 | 100 |
| Boc—Leu—Arg—Arg—MCA | 159 | 156 |
| Boc—Leu—Lys—Arg—MCA | 123 | 127 |
| Boc—Leu—Thr—Arg—MCA | 20.0 | 13.9 |
| Boc—Gly—Arg—Arg—MCA | 19.8 | 19.7 |
| Boc—Gly—Lys—Arg—MCA | 120 | 123 |
| Boc—Val—Pro—Arg—MCA | 107 | 88.0 |
| Boc—Asp(OBzl)—Pro—Arg—MCA | 12.3 | 7.8 |
| Boc—Ala—Gly—Pro—Arg—MCA | 1.9 | 1.6 |
| Boc—Leu—Ser—Thr—Arg—MCA | 127 | 97.0 |
| Boc—Glu—Lys—Lys—MCA | 1.3 | 0.9 |

Subsequently the effects of Benz-I on the following peptides (1) to (5) were examined. The composition of the employed reaction mixture and the examination conditions were as follows. Namely, 500 μl of a reaction mixture containing 25 μmol of tris hydrochloride buffer solution (pH 7.0), 0.25 μmol of CaCl$_2$, 5 mg of Lubrol PX, 100 μg of NaN$_3$, each peptide at various concentrations and Benz-I at various concentrations was allowed to react at 30° C. for 20 hours.

50-μl portions of the reaction mixture were sampled after the reaction for 0 and 20 hours and 50 μl of a reaction terminating agent comprising 0.2% of TFA and 10 mM of EDTA was added thereto. The resulting mixture was analyzed by HPLC. The HPLC was conducted by CH$_3$CN gradient elution with the use of an Ultron NC$_{18}$ column (0.45×15 cm) or a TSK gel ODS-80T$_M$ column (0.46×25 cm) in the presence of 0.1% of TFA.

Identification of new peak:

The residual reaction mixture was chromatographed under the same conditions as those employed in the above analysis and main peaks were fractionated. The fractionated eluate was evaporated to dryness on a centrifugal evaporator and decomposed with hydrochloric acid at 110° C. for 24 hours. Then each fragment was assumed from the amino acid composition.

(1) BAN-12P 200 mU of Benz-I was reacted with 50 nmol of BAM-12P (Tyr-Gly-Gly-Phe-Met-Arg-Arg-Val-Arg-Pro-Glu). After carrying out the reaction for 20 hours, peaks formed by chromatography were fractionated and the amino acid composition of each fraction was analyzed. As a result, it was found that a peak of a fragment assumed to have an amino acid composition of Glu: 1.24; Gly: 1.18; Val: 1.04; Arg: 1.10 and Pro: 0.916, namely, Val-Gly-Arg-Pro-Glu was obtained.

Thus it is presumed that Benz-I would cleave the linkage at the position shown by the arrow:

Tyr—Gly—Gly—Phe—Met—Arg—Val—Arg—Pro—Glu (2) Dynorphin A (1-13)

200 mU of Benz-I was reacted with 50 nmol of Dynorphin A (1-13) (Tyr-Gly-Gly-Phe-Leu-Arg-Arg-Ile-Arg-Pro-Lys-Leu-Lys). After carrying out the reaction for 20 hours, peaks formed by chromatography were fractionated and the amino acid composition of each fraction was analyzed. As a result, it was found that a peak of a fragment assumed to have an amino acid compositiom of Ile: 0.927; Leu: 1.18; Lys: 1.91; Arg: 1.06 and Pro: 0.919, namely Ile-Arg-Pro-Lys-Leu-Lys and a peak of a fragment assumed to have an amino acid composition of Gly: 2.36; Leu: 0.999; Tyr: 0.715; Phe: 1.11 and Arg: 1.82, namely, Try-Gly-Gly-Phe-Leu-Arg-Arg were obtained.

Thus it is presumed that Benz-I would cleave the linkage at the position shown by the arrow:

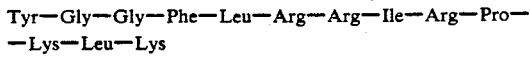
Tyr—Gly—Gly—Phe—Leu—Arg—Arg—Ile—Arg—Pro—
—Lys—Leu—Lys (3) Protein kinase-related peptide 200 mU of Benz-I was reacted with 50 nmol of protein kinase-related peptide (Arg-Lys-Arg-Ser-Arg-Lys-Glu). After carrying out the reaction for 20 hours, peaks formed by chromatography were fractionated and the amino acid composition of each fraction was analyzed. As a result, it was found that a peak of a fragment assumed to have an amino acid composition of Ser: 0.990; Glu: 1.03; Lys: 0.954 and Arg: 1.03, namely, Ser-Arg-Lys-Glu was obtained.

Thus it is presumed that Benz-I would cleave the position shown by the arrow:

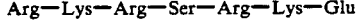
Arg—Lys—Arg—Ser—Arg—Lys—Glu (4) Xenopsin 200 mU of Benz-I was reacted with 50 nmol of Xenopsin (pGlu-Gly-Lys-Arg-Pro-Trp-Ile-Leu). After carrying out the reaction for 20 hours, peaks formed by chromatography were fractionated and the amino acid composition of each fraction was analyzed. As a result, it was found that a peak of a fragment assumed to have an amino acid composition of Glu: 0.993; Gly: 1.22; Lys: 0.674 and Arg: 1.11, namely, pGlu-Gly-Lys-Arg was obtained.

Thus it is presumed that Benz-I would cleave the linkage at the position shown by the arrow:

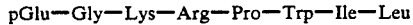
pGlu—Gly—Lys—Arg—Pro—Trp—Ile—Leu (5) 3200-dalton Adrenal Peptide E 200 mU of Benz-I was reacted with 25 nmol of 3200-dalton Adrenal Peptide E (Tyr-Gly-Gly-Phe-Met-Arg-Arg-Val-Gly-Arg-Pro-Glu-Trp-Trp-Met-Asp-Tyr-Gln-Lys-Arg-Tyr-Gly-Gly-Phe-Leu). After carrying out the reaction for 20 hours, peaks formed by chromatography were fractionated and the amino acid composition of each fraction was analyzed As a result, it was found that a peak of a fragment assumed to have an amino acid composition of Gly: 2.53; Met: 0.542; Tyr: 0.897; Phe: 1.03 and Arg: 2.00, namely, [1]Tyr-Gly-Gly-Phe-Met-Arg-[7]Arg, a peak of a fragment assumed to have an amino acid composition of Gly: 2.03; Leu: 1.01; Tyr: 0.913 and Phe: 1.04, namely, [21]Tyr-Gly-Gly-Phe-[25]Leu and a peak of a fragment assumed to have an amino acid composition of Asp: 0.764; Glu: 1.79; Gly: 3.29; Val: 1.01; Met: 1.26; Tyr: 2.07; Phe: 1.32; Lys: 1.17; Arg: 4.29 and Pro: 1.03, namely, Val-Gly-Arg-Pro-Glu-Trp-Trp-Met-Asp-Tyr-Gln-Lys-[20]Arg were obtained Thus it is presumed that Benz-I would cleave the linkages at the positions shown by the arrows:

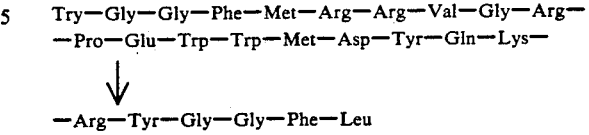
Try—Gly—Gly—Phe—Met—Arg—Arg—Val—Gly—Arg—
—Pro—Glu—Trp—Trp—Met—Asp—Tyr—Gln—Lys—
—Arg—Tyr—Gly—Gly—Phe—Leu

EXAMPLE 4

Optimum pH of protease specific for basic amino acid residue originating from *Kluyveromyces lactis* IFO 1903

Figure 8:
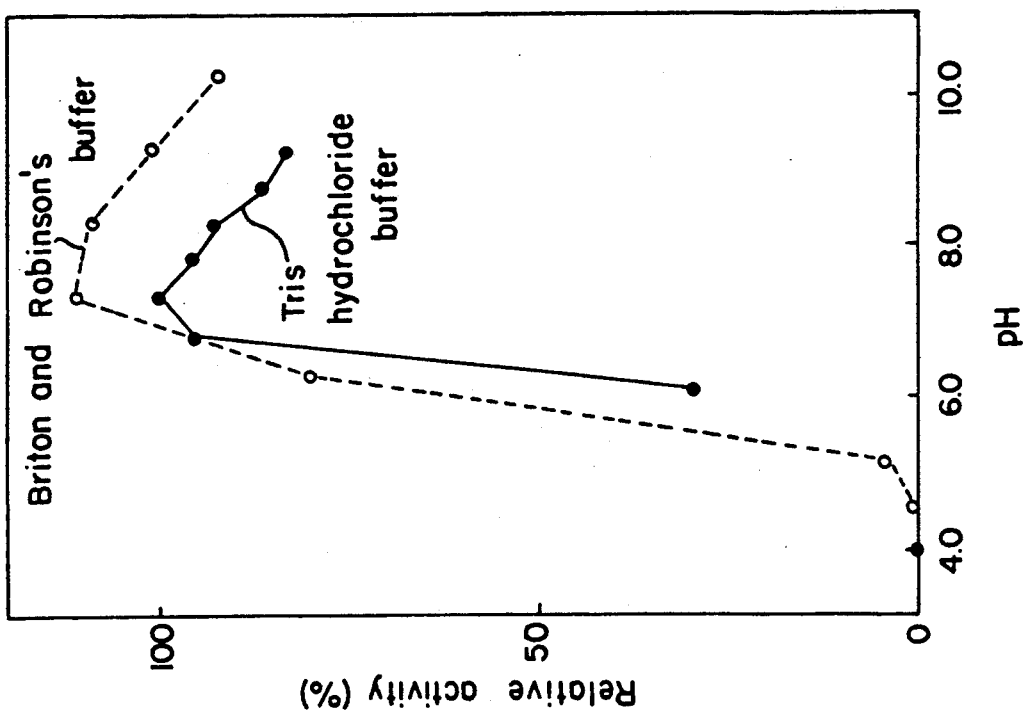
FIG. 8 shows the optimum pH values of Benz-I in tris hydrochloride buffer solution and Briton and Robinson's buffer solution.
Figure 7:
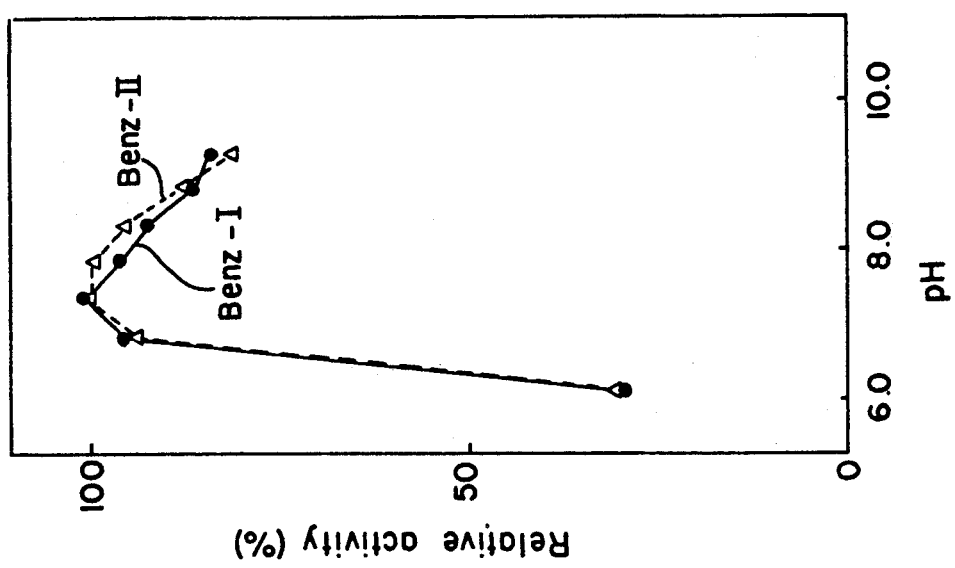
FIG. 7 shows the optimum pH values of Benz-I and Benz-II in tris hydrochloride buffer solution.

The activities of Benz-I and Benz-II were determined under standard reaction conditions while varying the type and pH of buffer solutions. As the buffer solutions, 50 mM tris hydrochloride buffer solution (pH 6 to 9) and 7.15 mM Briton and Robinson's buffer solution (pH 4 to 10) were employed. Each activity thus determined was expressed by the relative activity with the activity in tris hydrochloride buffer solution (pH 7.0) being 100. FIGS. 7 and 8 show the results.

EXAMPLE 5 pH stability of protease specific for basic amino acid residue originating from *Kluyveromyces lactis* IFO 1903

Figure 9:
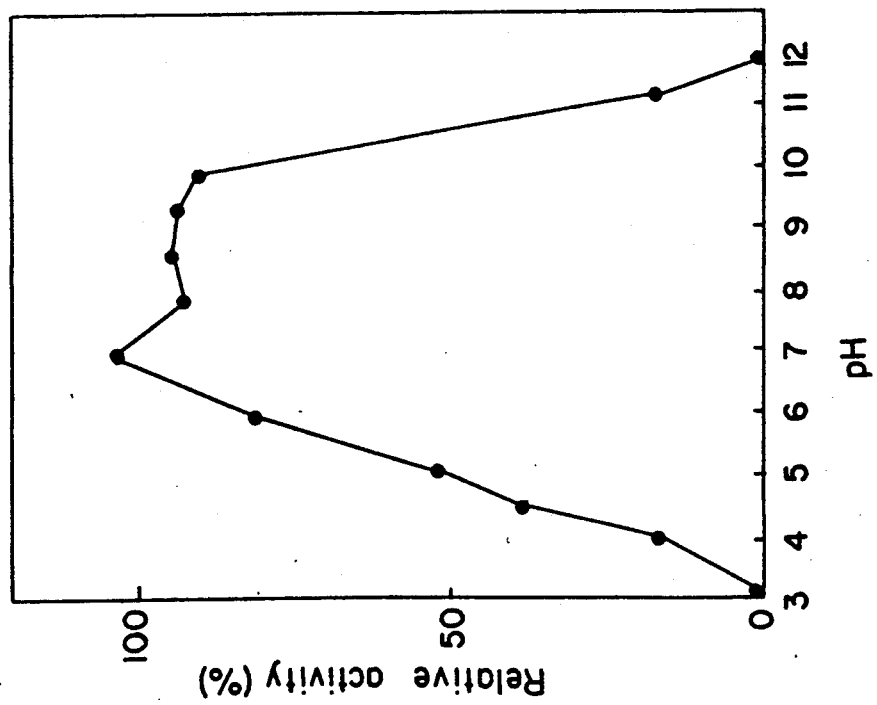
FIG. 9 shows the pH stability of Benz-I.

The enzyme (Benz-I) was incubated in 10.7 mM Briton and Robinson's buffer solution (pH 3 to 12) containing 0.2% of Lubrol PX and 0.5 mM of calcium chloride at 30° C. for 30 minutes. Then an equivalent amount of 100 mM tris hydrochloride buffer solution (pH 7.0) containing 0.2% of Lubrol PX and 0.5 mM of calcium chloride was added thereto to thereby adjust the pH value of the mixture to 7. The residual activity was determined under standard reaction conditions. FIG. 9 shows the residual activity after each treatment expressed by the relative activity determined with the activity of the control lot being 100.

EXAMPLE 6

Optimum temperature of protease specific for basic amino acid residue originating from *Kluyveromyces lactis* IFO 1903

Figure 10:
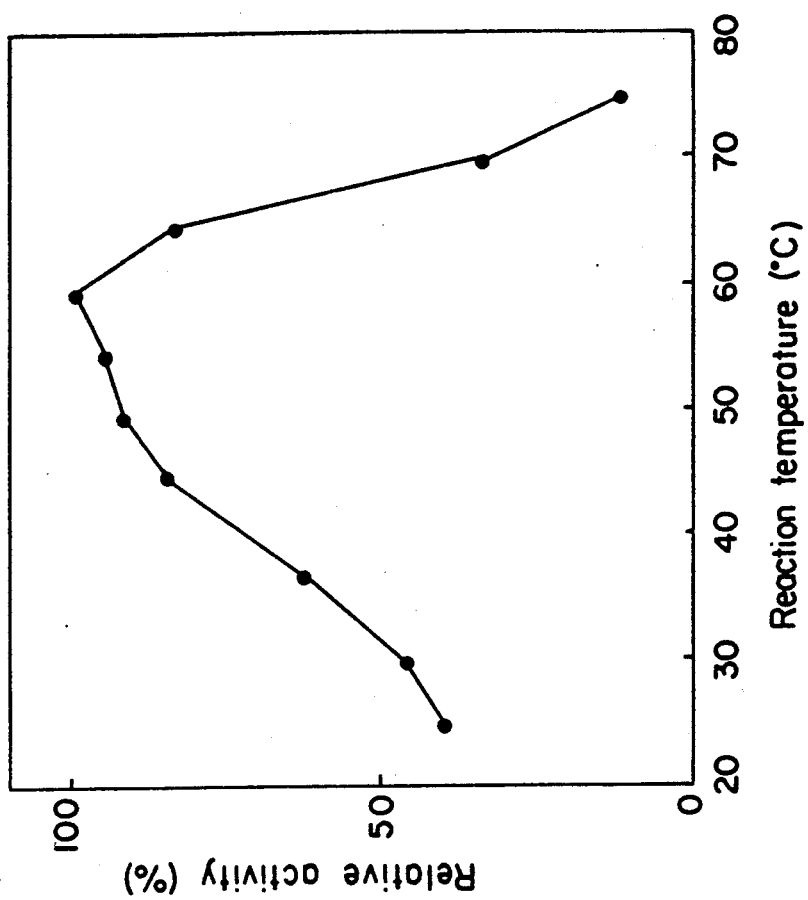
FIG. 10 shows the optimum temperature of Benz-I.

The activity of Benz-I was determined under standard conditions except varying the reaction temperature from 25° to 75° C. FIG. 10 shows the activity at each temperature expressed by the relative activity determined with the activity at 60° C. being 100.

EXAMPLE 7

Temperature stability of protease specific for basic amino acid residue originating from *Kluyveromyces lactis* IFO 1903

Figure 11:
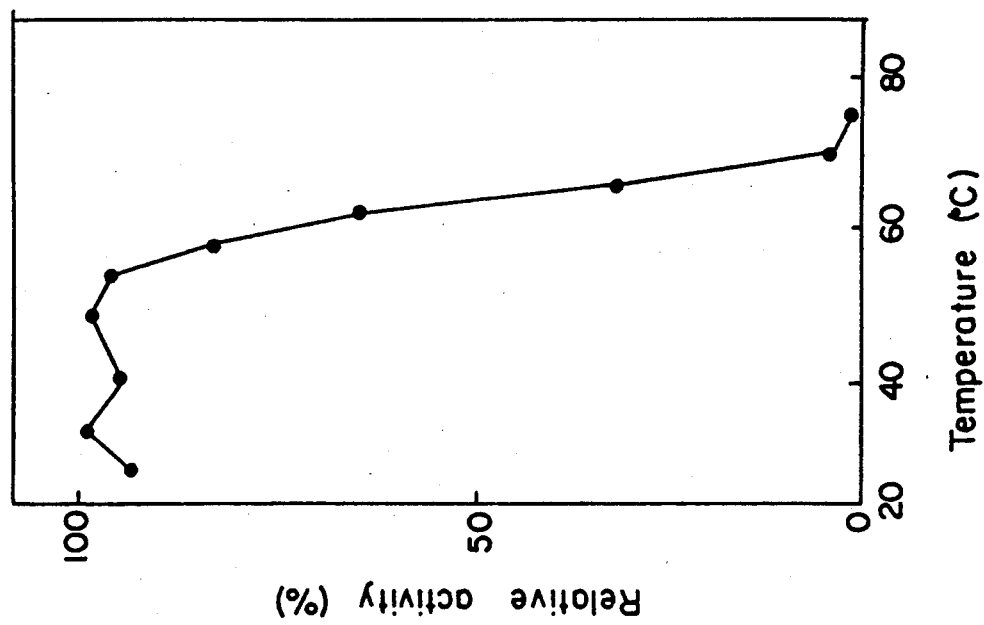
FIG. 11 shows the heat stability of Benz-I.

The enzyme Benz-I was incubated at various temperatures for ten minutes and then quenched in ice water. The residual activity after each treatment was determined under standard reaction conditions. FIG. 11 shows each residual activity expressed by the relative activity determined with the activity of the control lot being 100.

EXAMPLE 8

Behavior of protease specific for basic amino acid residue originating from *Kluyveromyces lactis* IFO 1903 against various inhibitors The enzymes Benz-I and Benz-II were incubated in the absence of any substrate in standard reaction mixtures containing various inhibitors at 25° C. for 30 minutes. After adding the substrate, the residual activity of each enzyme was determined. Table 4 shows the residual activity of each case expressed by the relative activity determined with the activity of the control lot being 100.

TABLE 4

Behavior of protease specific for basic amino acid residue originating from *Kluyveromyces lactis* IFO against inhibitors

| Inhibitor | Conc. | Benz-I | Benz-II |
|---|---|---|---|
| control | — | 100 | 100 |
| diisopropyl fluorophosphate (DFP) | 1 mM | 115 | 114 |
| phenylmethanesulfonyl fluoride (PMSF) | 1 mM | 107 | 103 |
| p-amidino-PMSF | 1 mM | 0 | 0 |
| tosyllysine chloromethyl ketone (TLCK) | 0.2 mM | 98 | 95 |
| p-chloromercuribenzoic acid (pCMB) | 50 μM | 1 | 3 |
| iodoacetic acid (MIA) | 1 mM | 99 | 93 |
| iodoacetamide (IAA) | 1 mM | 92 | 87 |
| N-ethylmaleimide | 1 mM | 101 | 94 |
| leupeptin | 10 μM | 93 | 96 |
| antipain | 10 μM | 89 | 88 |
| E-64 | 10 μM | 99 | 96 |
| chymostatin | 10 μM | 98 | 99 |
| diazoacetyl-DL-norleucine methyl ester (DAN) | 5 mM | 85 | 73 |
| pepstatin A | 10 μM | 100 | 96 |
| ethylenediaminetetraacetic acid (EDTA) | 1 mM | 6 | 6 |
| ethylenediaminetetraacetic acid (EDTA) | 5 mM | 1 | 2 |
| ethylene glycol bis(2-aminoethyl ether)tetraacetic acid (EGTA) | 1 mM | 53 | 43 |
| ethylene glycol bis(2-aminoethyl ether)tetraacetic acid (EGTA) | 5 mM | 12 | 12 |
| o-phenanthroline (o-PT) | 1 mM | 96 | 86 |
| phosphoramidon | 10 μM | 101 | 93 |
| benzamidine | 1 mM | 79 | 82 |
| bestatin | 10 μM | 95 | 97 |
| dithiothreitol (DTT) | 1 mM | 96 | 128 |
| 2-mercaptoethanol (2-ME) | 1 mM | 112 | 153 |
| zinc chloride | 1 mM | 7 | 7 |
| copper sulfate | 1 mM | 0.2 | 0.6 |
| mercury chloride | 1 mM | 0 | 0 |
| urea | 4 M | 23 | 29 |
| sodium dodecyl sulfate (SDS) | 0.1% | 94 | 91 |

EXAMPLE 9

Effects of various metal ions in the recovery of the activity of protease specific for basic amino acid residue originating from *Kluyveromyces lactis* IFO 1903

Benz-I was incubated in the presence of 10 mM of EDTA at 4° C. for one hour. When the enzyme was completely inactivated, the culture was dialyzed against 10 mM tris hydrochloride buffer solution (pH 7.0) containing 0.2% of Lubrol PX to thereby completely remove the EDTA. The enzyme mixture thus dialyzed was examined with respect to the recovery of the activity in reaction mixtures containing 0.5 mM of various metal ions. Table 5 shows the activity of each case expressed by the relative activity determined with the activity of the control lot being 100.

TABLE 5

Effects of various metal ions on the recovery of the activity of protease specific for basic amino acid residue originating from *Kluyveromyces lactis* IFO 1903

| | Reaction mixture | | Relative activity (%) |
|---|---|---|---|
| | EDTA | Metal ion | |
| control | — | calcium chloride | 100 |
| treated with EDTA | — | — | 0.36 |
| treated with EDTA | 10 mM | — | 0.09 |
| dialyzed | — | — | 47.6 |
| dialyzed | — | calcium chloride | 93.1 |
| dialyzed | — | magnesium chloride | 43.6 |
| dialyzed | — | manganese chloride | 33.9 |
| dialyzed | — | nickel chloride | 16.1 |
| dialyzed | — | cobalt chloride | 21.1 |

EXAMPLE 10

Effect of calcium ion concentration on the activity of protease specific for basic amino acid residue originating from Kluyveromyces lactis IFO-1903

Figure 12:
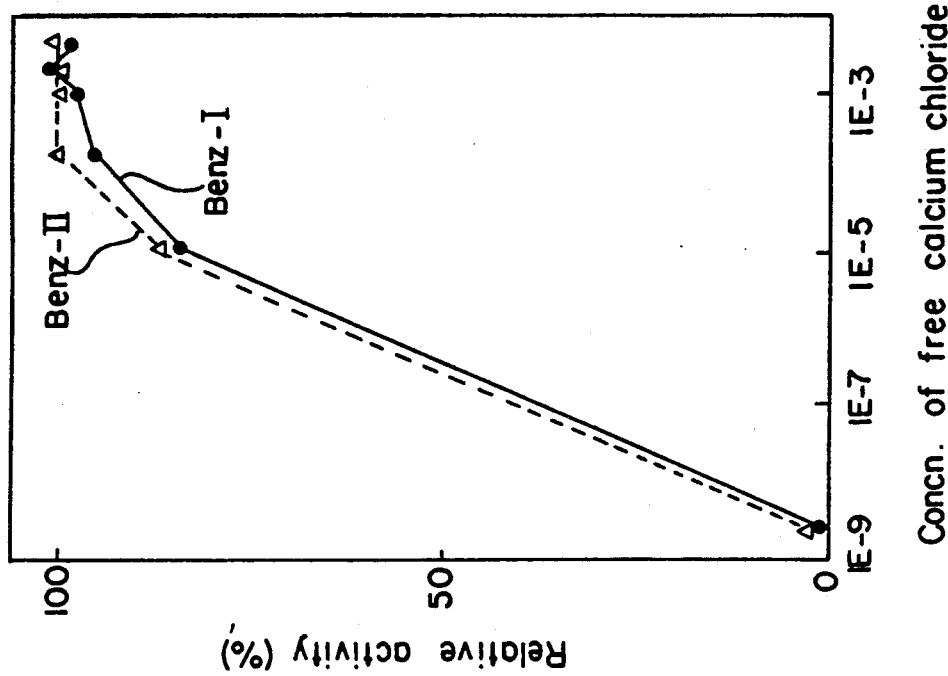
FIG. 12 shows the effects of free calcium chloride concentration on the activities of Benz-I and Benz-II.

The activities of Benz-I and Benz-II were determined in a standard reaction mixture containing 0.1 mM of EDTA while varying the concentration of calcium chloride. The concentration of free calcium chloride was calculated from the apparent dissociation constant $K_1$ (log $K_1$=7.3). FIG. 12 shows the activity of each enzyme at each calcium chloride concentration expressed by the relative activity determined with the activity at 1 mM being 100.

EXAMPLE 11

Effect of Lubrol PX on the activity of protease specific for basic amino acid residue originating from *Kluyveromyces lactis* IFO 1903

Figure 13:
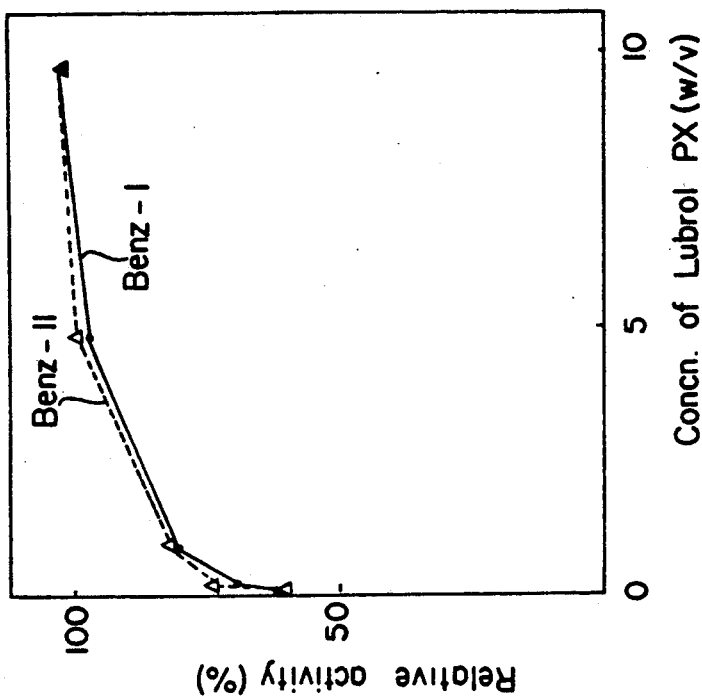
FIG. 13 shows the effects of Lubrol PX concentration on the activities of Benz-I and Benz-II.

The activities of Benz-I and Benz-II were determined under standard reaction conditions except that the Lubrol PX concentration was varied. FIG. 13 shows the activity at each Lubrol PX concentration expressed by the relative activity determined with the maximum activity being 100.

EXAMPLE 12

Molecular weight of protease specific for basic amino acid residue originating from *Kluyveromyces lactis* IFO 1903

The molecular weights of Benz-I and Benz-II were determined by gel filtration by using TSK gel G 3000 SW$_{XL}$ (0.78×30 cm) free from any surfactant. As a result, the molecular weight of Benz-I was found to be approximately 60,000 to 100,000 while that of Benz-II to be approximately 100,000.

EXAMPLE 13

Partial purification of protease specific for basic amino acid residue in membrane extract obtained in Example 1.

Figure 14:
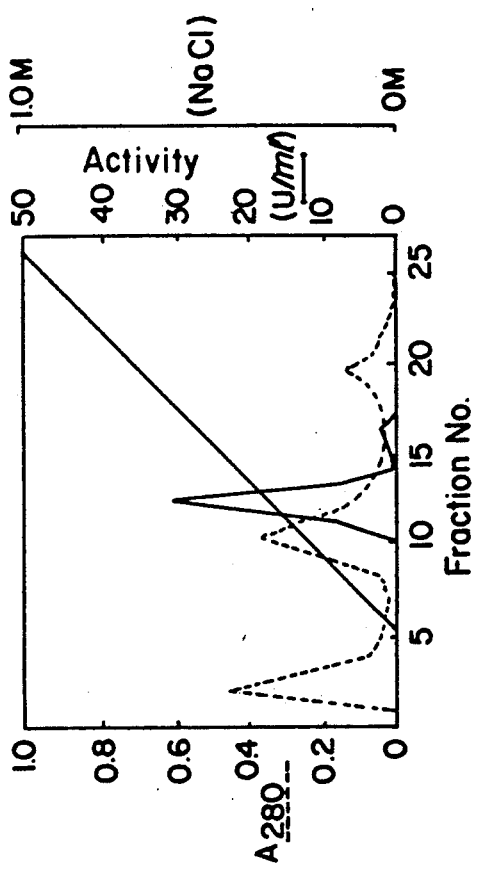
FIG. 14 is a Mono Q chromatogram of the membrane extract obtained from Rhodosporidium IFO 0413.
Figure 15:
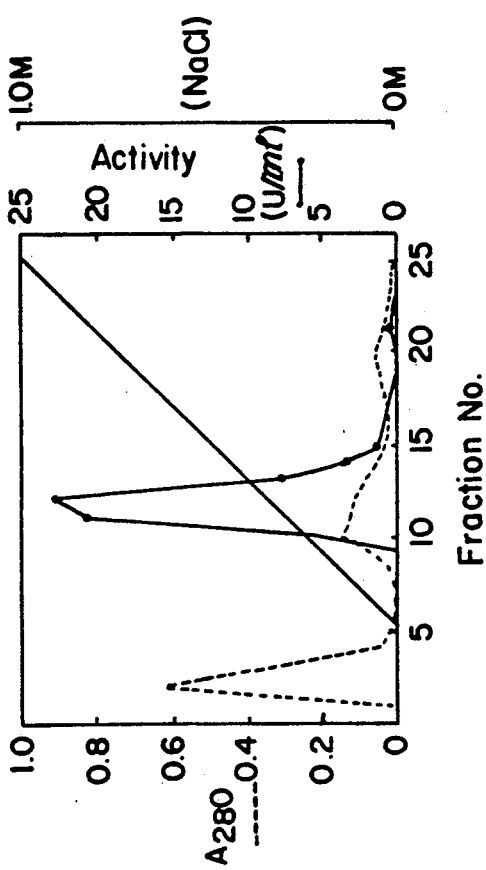
FIG. 15 is a Mono Q chromatogram of the membrane extract obtained from Hansenula IFO 0980.

Part of each of the membrane extracts prepared from Rhodosporidium IFO 0413 and Hansenula IFO 0980 in Example 1 was dialyzed against the buffer solution 1 (10 mM tris hydrochloride buffer solution, pH 7.0, containing 0.5 mM of calcium chloride and 0.2% of Lubrol PX) and poured into a Mono Q column (0.5×5.0 cm, mfd. by Pharmacia AB) which had been equilibrated with said buffer solution. After throughly washing the column with said buffer solution, the enzyme was eluted by gradient elution with the use of 0 to 0.1M sodium chloride. FIGS. 14 and 15 show the chromatograms of Rhodosporidum IFO 0413 and Hansenula IFO 0980, respectively. The active fractions thus obtained were collected and the specific activities thereof were determined. Table 6 shows the specific activity thus determined as well as that determined prior to the chromatography.

TABLE 6

Partial purification of protease specific for basic amino acid residue with Mono Q

| Strain | Specific activity (U/mg) | |
|---|---|---|
| | membrane extract | Mono Q |
| Rhodosporidium IFO 0413 | 0.342 | 4.19 |
| Hansenula IFO 0980 | 0.457 | 3.14 |

EXAMPLE 14

Substrate specificity of partially purified enzyme

The relative activities of the enzymes purified in Example 13 for Boc-Gln-Arg-Arg-MCA, Boc-Ile-Glu-Gly-Arg-MCA and Pro-Phe-Arg-MCA were determined. Table 7 shows the results. The determination was carried out under standard reaction conditions with the use of a mixture containing 100 μM of each substrate. Each relative activity was determined with the activity for Boc-Gln-Arg-Arg-MCA being 100.

TABLE 7

Substrate specificity of partially purified enzyme

| Strain | Relative activity (%) | | |
|---|---|---|---|
| | A | B | C |
| Rhodosporidium IFO 0413 | 100 | 1.2 | trace |
| Hansenula IFO 0980 | 100 | 11.3 | trace |

Note:
A, B and C represent Boc—Gln—Arg—Arg—MCA, Boc—Ile—Glu—Gly—Arg—MCA and Pro—Phe—Arg—MCA, respectively.

EXAMPLE 15

Purification of protease specific for basic amino acid residue from *Sporobolomyces odrus* IFO 1597

*Sporobolomyces odrus* IFO 1597 was cultured in 33 l of a YM medium containing 10 g/l of glucose, 5 g/l of bactopeptone, 3 g/l of yeast extract and 3 g/l of malt extract for two days. Then the culture medium was centrifuged to thereby collect 265 g (moist weight) of cells. These cells were suspended in 300 ml of a buffer solution 1 (10 mM tris hydrochloride buffer solution, pH 7.0, containing 0.5 mM of calcium chloride) and ground with a DYNA-MILL. Then the mixture was centrifuged at 1,000 g for ten minutes to thereby remove residual cells. The obtained supernatant was ultracentrifuged at 150,000 g for 60 minutes. Thus a membrane fraction was obtained as the precipitate. The membrane fraction was suspended in 60 ml of an extraction buffer solution (10 mM tris hydrochloride buffer solution, pH 7.0, containing 0.05 mM of $CaCl_2$, 1% of Lubrol PX and 0.1M of NaCl) and stirred overnight to thereby extract the enzyme. After ultracentrifuging under the same conditions as those described above, a membrane extract was obtained as the supernatant.

To the membrane extract was added ammonium sulfate to achieve 30% saturation and the resulting mixture was centrifuged at 6,000 g for 20 minutes. To the supernatant thus obtained was further added ammonium sulfate to achieve 70% saturation. The resulting mixture was centrifuged at 6,000 g for 20 minutes and the precipitate was collected as a 30–70% ammonium sulfate fraction.

This precipitate was dissolved in a small amount of a buffer solution 2 (10 mM tris hydrochloride buffer solution, pH 8.0, containing 0.5 mM of $CaCl_2$ and 0.2% of Lubrol PX) and dialyzed against the same buffer solution. Then it was heated to 50° C. for ten minutes. The precipitate thus formed was removed by centrifuging at 39,000 g for 20 minutes to thereby give a heat-treated fraction.

Figure 16:
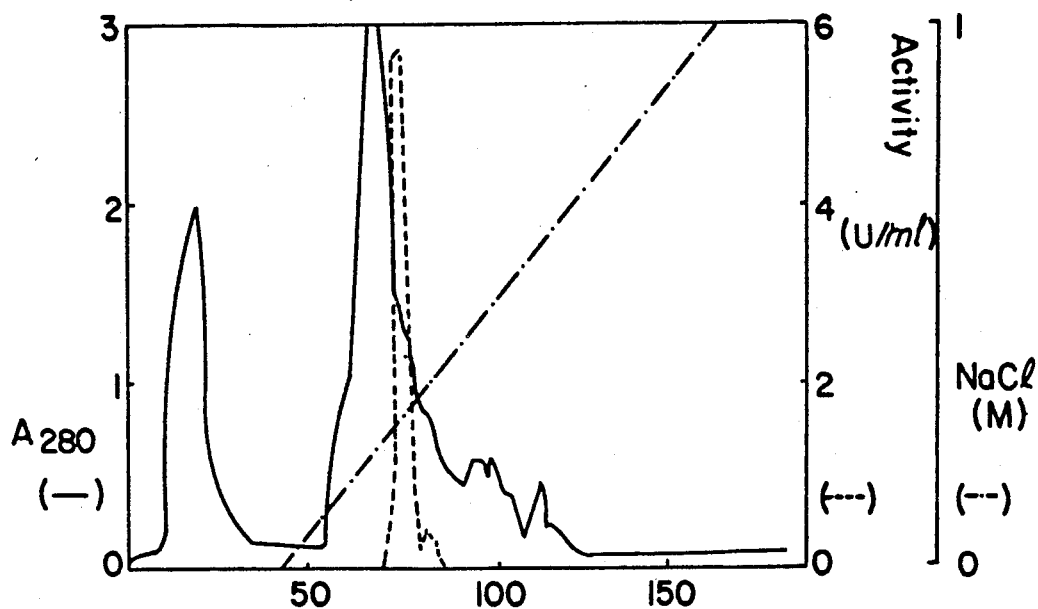
FIG. 16 is a DEAE/Toyopearl 650 M chromatogram formed in the purification of a protease specific for a basic amino acid residue originating from *Sporobolomyces odrus* IFO 1597.

This fraction was poured into a DEAE/Toyopearl 650M column (mfd. by Toso Co., Ltd., 2.5×40 cm) which had been preliminarily equilibrated with the buffer solution 2 (pH 8.0). After thoroughly washing the column with said buffer solution, the enzyme was eluted by gradient elution with 0 to 1M sodium chloride to thereby give an active fraction. FIG. 16 shows the elution pattern.

Figure 17:
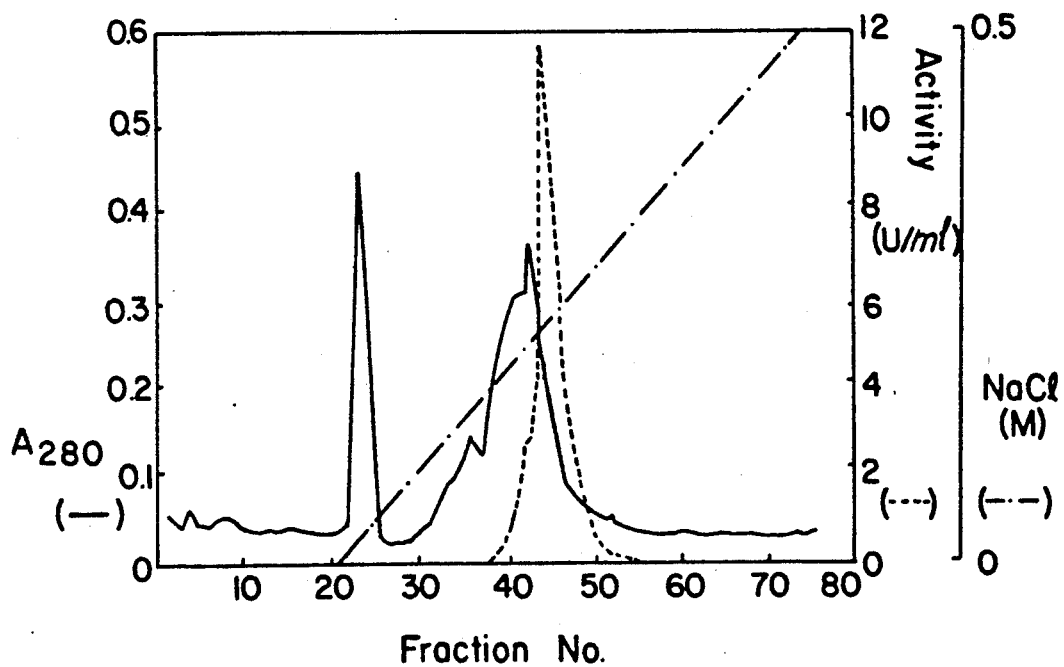
FIG. 17 is an Arg/Sepharose chromatogram of a protease specific for a basic amino acid residue originating from *Sporobolomyces odrus* IFO 1597.

The active fraction was concentrated by ultrafiltration, dialyzed against the buffer solution 2 (pH 7.0) and then poured into an arginine/Sepharose column (mfd. by Pharmacia AB; 2.5×10 cm) which had been preliminarily equilibrated with the buffer solution 2. After thoroughly washing the column with said buffer solution, the enzyme was eluted by gradient elution with the use of 0 to 0.5M of NaCl. FIG. 17 shows the elution pattern. The active fraction was concentrated and referred to as the Arg/Sepharose fraction.

The Arg/Sepharose fraction was poured into a Con A/Sepharose column (mfd. by Pharmacia AB; 1.6×25 cm), which had been preliminarily equilibrated with said buffer solution 2 (pH 7.0) containing 0.5M of NaCl. After thoroughly washing the column with said buffer solution, the enzyme was eluted with the buffer solution 2 (pH 7.0) containing 0.5M of NaCl and 0.5M of α-methyl-D-mannoside. The active fraction was concentrated and referred to as the Con A/Sepharose fraction.

The Con A/Sepharose fraction was dialyzed against the buffer solution 1 (pH 7.0) and poured into a Mono Q column (mfd. by Pharmacia AB) which had been equilibrated with said buffer solution. Then it was eluted by gradient elution with the use of 0 to 0.6M of NaCl. The active fraction was concentrated and referred to as the Mono Q fraction.

The Mono Q fraction was gel-filtered through Superose 12 (mfd. Pharmacia AB) which had been equilibrated with the buffer solution 1 (pH 7.0). The active fraction thus obtained was concentrated and referred to as the Superose 12 fraction. The enzyme thus purified was homogeneous when examined by gel filtration and SDS/PAGE.

Table 7 summarizes the results of purification.

TABLE 7

Purification of protease specific for basic amino acid residue from *Sporobolomyces odrus* IFO 1597

| Step | Volume (ml) | Protein (mg) | Activity (U) | Specific activity (U/mg) | Yield (%) | Purification ratio |
|---|---|---|---|---|---|---|
| membrane extraction | 1,000 | 12,900 | 926 | 0.0718 | 100 | 1 |
| 30–70% ammonium sulfate fracture | 75.0 | 2,720 | 740 | 0.272 | 80 | 4 |
| heat-treated fraction | 1.0 | 1,320 | 628 | 0.475 | 68 | 7 |

TABLE 7-continued

Purification of protease specific for basic amino acid residue from *Sporobolomyces odrus* IFO 1597

| Step | Volume (ml) | Protein (mg) | Activity (U) | Specific activity (U/mg) | Yield (%) | Purification ratio |
|---|---|---|---|---|---|---|
| DEAE/Toyopearl fraction | 23.0 | 66.9 | 320 | 4.78 | 35 | 66 |
| Arg/Sepharose fraction | 3.1 | 9.9 | 263 | 26.5 | 28 | 367 |
| Con A/Sepharose fraction | 3.0 | 2.2 | 124 | 56.3 | 13 | 789 |
| Mono Q fraction | 1.4 | 0.42 | 49.3 | 116 | 5.3 | 1620 |
| Superose 12 fraction | 0.65 | 0.095 | 12.9 | 136 | 1.4 | 1900 |

EXAMPLE 16

Substrate specificity of protease specific for basic amino acid residue

The activities of the enzyme for various fluorescent substrates were determined under standard reaction conditions. Table 8 shows the activity for each substrate expressed by the relative activity determined with the activity for Boc-Gln-Arg-Arg-MCA being 100.

TABLE 8

Substrate specificity of protease specific for basic amino acid residue

| Substrate | Activity (%) | Substrate | Activity (%) |
|---|---|---|---|
| Boc—Gln—Arg—Arg—MCA | 100 | Pro—Phe—Arg—MCA | 0 |
| Boc—Leu—Arg—Arg—MCA | 115 | Z—Arg—Arg—MCA*[1] | 0 |
| Boc—Leu—Lys—Arg—MCA | 75 | Bz—Arg—MCA*[2] | 0 |
| Boc—Leu—Thr—Arg—MCA | 3 | Boc—Glu—Lys—Lys—MCA | 0 |
| Boc—Leu—Gly—Arg—MCA | 1 | Boc—Val—Leu—Lys—MCA | 0 |
| Boc—Gly—Arg—Arg—MCA | 32 | Arg—MCA | <1 |
| Boc—Gly—Lys—Arg—MCA | 59 | Leu—MCA | <1 |
| Boc—Val—Pro—Arg—MCA | 26 | Suc—Gly—Pro—MCA*[3] | 0 |
| Boc—Asp(OBzl)—Pro—Arg—MCA*[4] | 5 | Suc—Ala—Pro—Ala—MCA | 0 |
| Boc—Ala—Gly—Pro—Arg—MCA | 1 | Suc—Leu—Leu—Val—Tyr—MCA | 0 |
| Boc—Ile—Glu—Gly—Arg—MCA | 5 | Suc—Ala—Ala—Pro—Phe—MCA | <1 |
| Boc—Leu—Ser—Thr—Arg—MCA | 2 | | |

Note:
*[1]X represents a benzyloxycarbonyl group.
*[2]Bz represents a benzoyl group.
*[3]Suc represents a succinyl group.
*[4]Asp(OBzl) represents a group where the β-carboxyl group of aspartic acid is protected with a benzyl ester.

EXAMPLE 17

Optimum pH value of protease specific for basic amino acid residue

Figure 18:
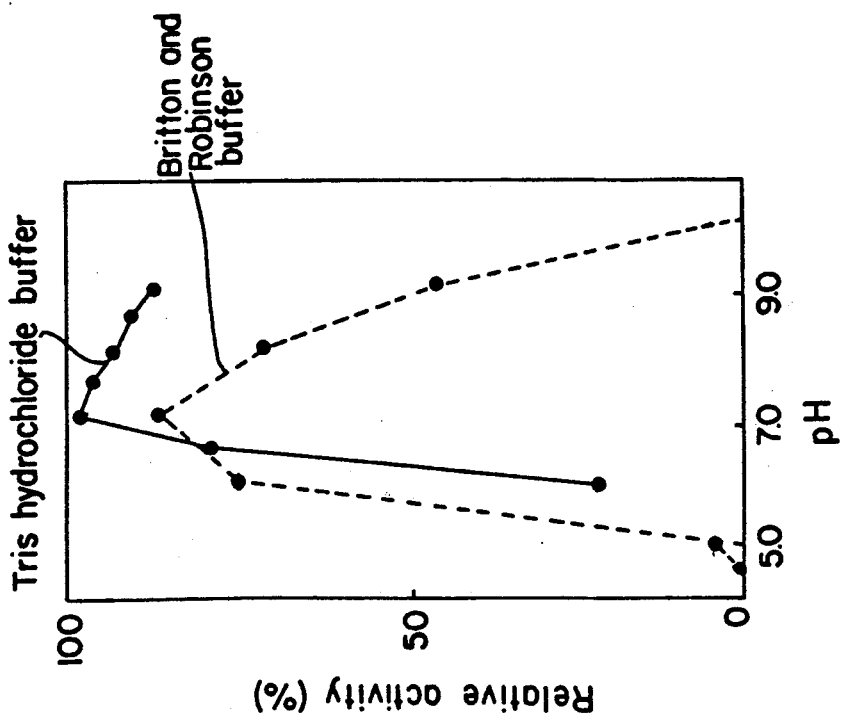
FIG. 18 shows the optimum pH values of the protease specific for a basic amino acid residue of the present invention.

The activity of the enzyme was determined under standard reaction conditions while varying the type and pH of buffer solutions. As the buffer solutions, 50 mM tris hydrochloride buffer solution (pH 6.0 to 9.0) and 7.15 mM Briton and Robinson's buffer solution (pH 4.5 to 10.0) were employed. Each activity thus determined was expressed by relative activity with the activity in tris hydrochloride buffer solution (pH 7.0) being 100. FIG. 18 shows the results.

EXAMPLE 18 pH stability of protease specific for basic amino acid residue

Figure 19:
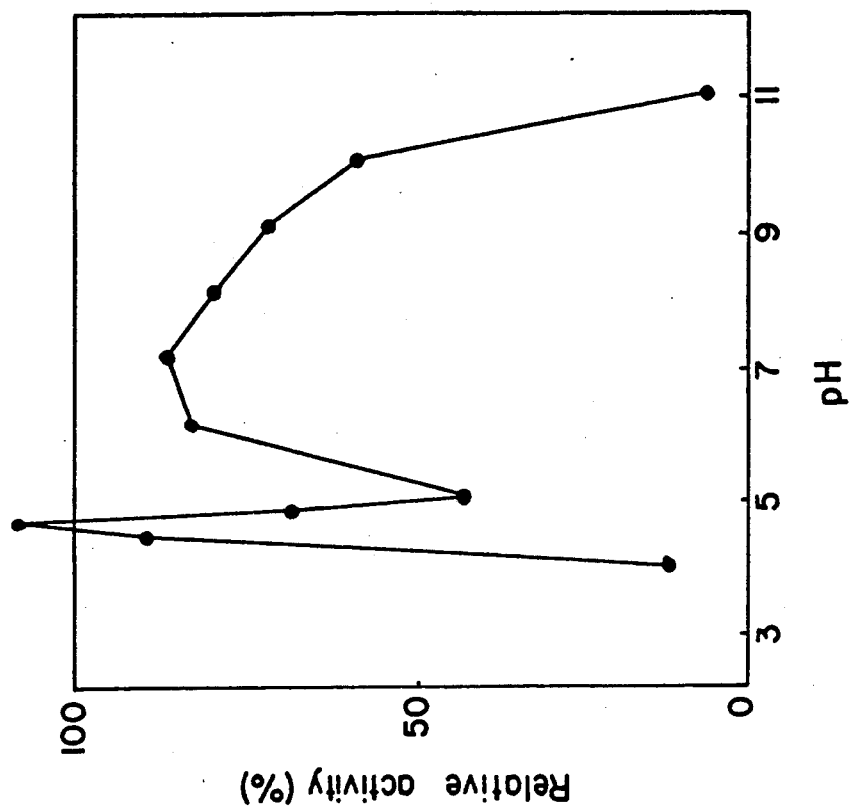
FIG. 19 shows the pH stability of the protease specific for a basic amino acid residue of the present invention.

The enzyme was incubated in 11.9 mM Briton and Robinson's buffer solution (pH 4 to 11) containing 0.2% of Lubrol PX and 0.5 mM of calcium chloride at 30° C. for 30 minutes. Then an equivalent amount of 100 mM tris hydrochloride buffer solution (pH 7.0) was added thereto to thereby adjust the pH value of the mixture to 7. The residual activity was determined under standard reaction conditions. FIG. 19 shows the residual activity after each treatment expressed by the relative activity determined with the activity of the control lot being 100.

EXAMPLE 19

Optimum temperature of protease specific for basic amino acid residue

Figure 20:
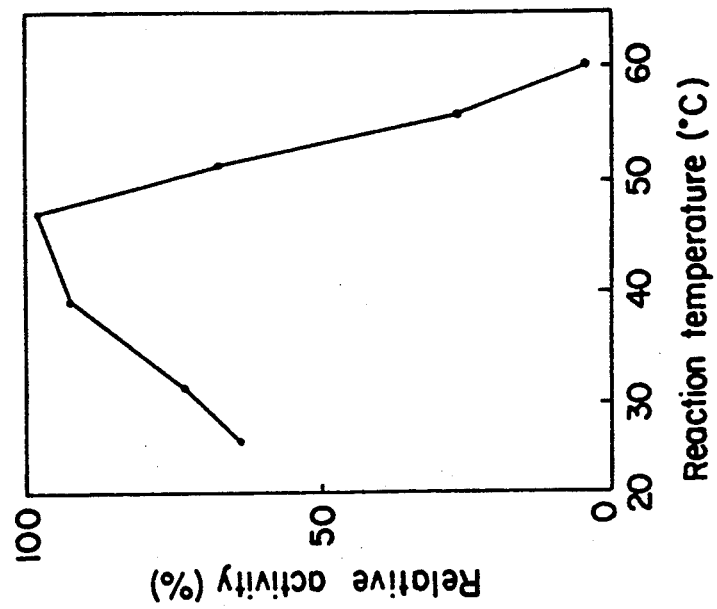
FIG. 20 shows the optimum temperature of the protease specific for a basic amino acid residue of the present invention.

The activity of the enzyme was determined under standard conditions except varying the reaction temperature from 25° to 75° C. FIG. 20 shows the activity at each temperature expressed by the relative activity determined with the activity at 45° C. being 100.

EXAMPLE 20

Heat stability of protease specific for basic amino acid residue

Figure 21:
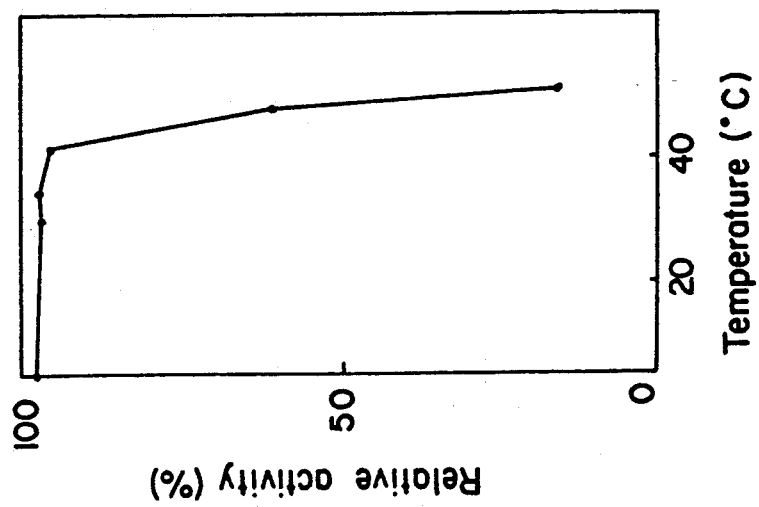
FIG. 21 shows the heat stability of the protease specific for a basic amino acid residue of the present invention.

The enzyme was incubated at various temperatures for ten minutes and then quenched in ice water. The residual activity after each treatment was determined under standard reaction conditions. FIG. 21 shows each residual activity expressed by the relative activity determined with the activity of the control lot being 100.

EXAMPLE 21

Behavior of protease specific for basic amino acid residue against various inhibitors The enzymes was incubated in the absence of any substrate in standard reaction mixtures containing various inhibitors at 25° C. for 30 minutes. After adding the substrate, the residual activity of each enzyme was determined. Table 9 shows the residual activity of each case expressed by the relative activity determined with the activity of the control lot being 100.

TABLE 9
Behavior of protease specific for basic amino acid residue against inhibitors

| Inhibitor | $Ca^{2+}$ | Concn. | relative activity (%) |
|---|---|---|---|
| Control-1 | + | — | 100 |
| Control-2 | — | — | 55 |
| Serine protease inhibitor: | | | |
| diisopropyl fluorophosphate (DFP) | + | 1 mM | 129 |
| phenylmethanesulfonyl fluoride (PMSF) | + | 1 mM | 112 |
| p-amidino-PMSF (p-APMSF) | + | 1 mM | 10 |
| tosyllysine chloromethyl ketone (TLCK) | + | 0.2 mM | 108 |
| Cysteine protease inhibitor: | | | |
| p-chloromercuribenzoic acid (pCMB) | + | 50 μM | 36 |
| iodoacetamide (IAA) | + | 1 mM | 96 |
| N-ethylmaleimide (NEM) | + | 1 mM | 125 |
| leupeptin | + | 10 μM | 92 |
| antipain | + | 10 μM | 70 |
| E-64 | + | 10 μM | 100 |
| Aspartic protease inhibitor: | | | |
| pepstatin A | + | 10 μM | 104 |
| diazoacetyl-DL-norleucine methyl ester (DAN) | + | 5 mM | 72 |
| Metal protease inhibitor: | | | |
| ethylenediaminetetraacetic acid (EDTA) | — | 1 mM | 2 |
| ethylene glycol bis(2-aminoethyl ether)-tetraacetic acid (EGTA) | — | 1 mM | 10 |
| o-phenanthroline | — | 1 mM | 91 |
| phosphoramidon | + | 10 μM | 100 |
| Others: | | | |
| banzamidine | + | 1 mM | 82 |
| bestatin | + | 10 μM | 97 |
| chymostatin | + | 10 μM | 98 |
| dithiothreitol (DTT) | + | 1 mM | 97 |
| β-mercaptoethanol (β-ME) | + | 1 mM | 95 |
| $ZnCl_2$ | + | 1 mM | 1 |
| $CuCO_4$ | + | 1 mM | 2 |
| $HgCl_2$ | + | 1 mM | 0 |

EXAMPLE 22

Figure 22:
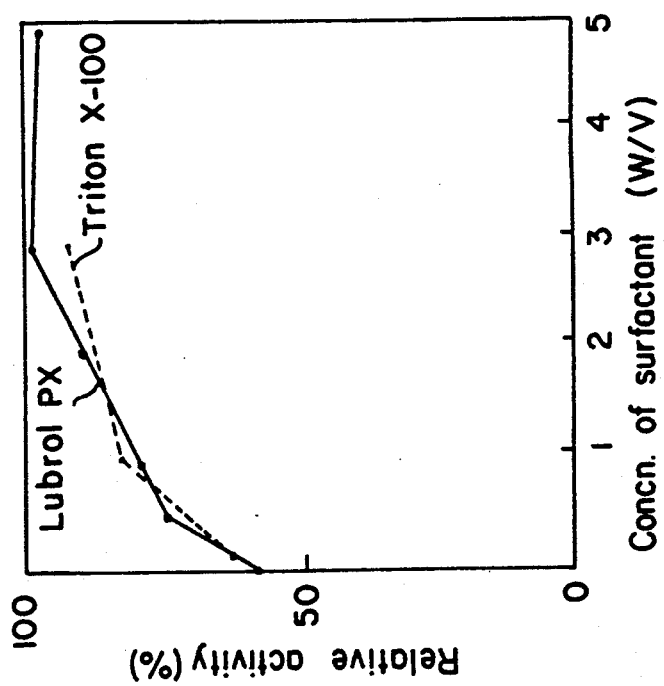
FIG. 22 shows the effects of surfactants on the activity of the protease specific for a basic amino acid residue of the present invention.

Effect of surfactant on the activity of protease specific for basic amino acid residue The enzyme was reacted in the standard reaction mixture while varying the type and concentration of surfactants. FIG. 22 shows each activity expressed by the relative activity determined with the activity in the presence of 3% Lubrol PX being 100.

EXAMPLE 23

Figure 23:
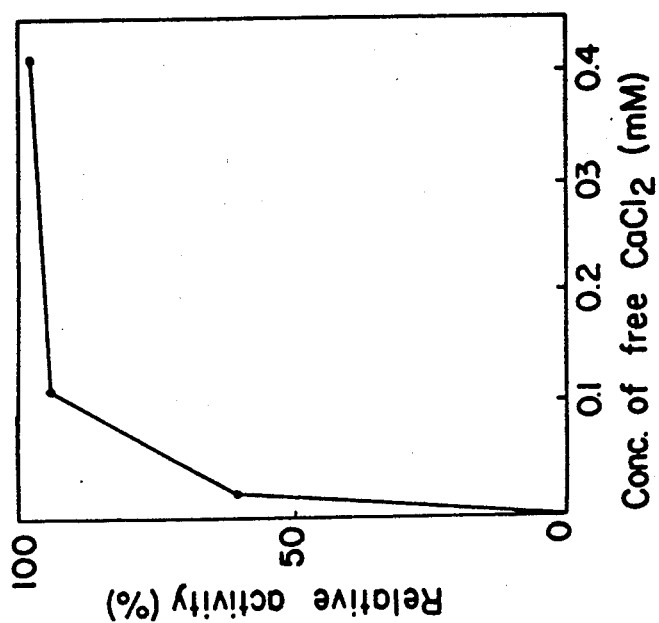
FIG. 23 shows the effect of $CaCl_2$ on the activity of the protease specific for a basic amino acid residue of the present invention.

Effect of calcium chloride on the activity of protease specific for basic amino acid residue The activity of the enzyme was determined in the presence of 0.1% of EDTA while varying the concentration of $CaCl_2$. FIG. 23 shows each activity expressed by the relative activity determined with the activity in the presence of 0.5 mM of $CaCl_2$ being 100. The concentration of free $CaCl_2$ was calculated from the apparent dissociation constant ($K_1$) of EDTA for $CaCl_2$ (log $K_1 = 7.3$).

EXAMPLE 24

Effect of various metal ions on the recovery of the activity of protease specific for basic amino acid residue treated with EDTA The enzyme was treated in the standard reaction mixture containing 1 mM of EDTA and free from any substrate at 25° C. for 30 minutes. Various metal ions were added thereto each in such an amount as to give a concentration of 1.5 mM and the mixture was incubated at 30° C. for five minutes. Then the activity of each case was determined. Table 10 shows each activity expressed by the relative activity determined with the activity in the control lot being 100.

TABLE 10
Effect of various metal ions on the recovery of the activity of protease specific for basic amino acid residue treated with EDTA

| No. | EDTA treatment | Reaction system | | Relative activity (%) |
|---|---|---|---|---|
| | | EDTA (1 mM) | Metal (1.5 mM) | |
| 1 | — | — | $CaCl_2$ (0.5 mM) | 100 |
| 2 | + | + | — | 0 |
| 3 | + | — | — | 3 |
| 4 | + | + | $CaCl_2$ | 107 |
| 5 | + | + | $MgCl_2$ | 12 |
| 6 | + | + | $CoCl_2$ | 57 |
| 7 | + | + | $NiCl_2$ | 58 |
| 8 | + | + | $MnCl_2$ | 53 |

EXAMPLE 25

Figure 25:
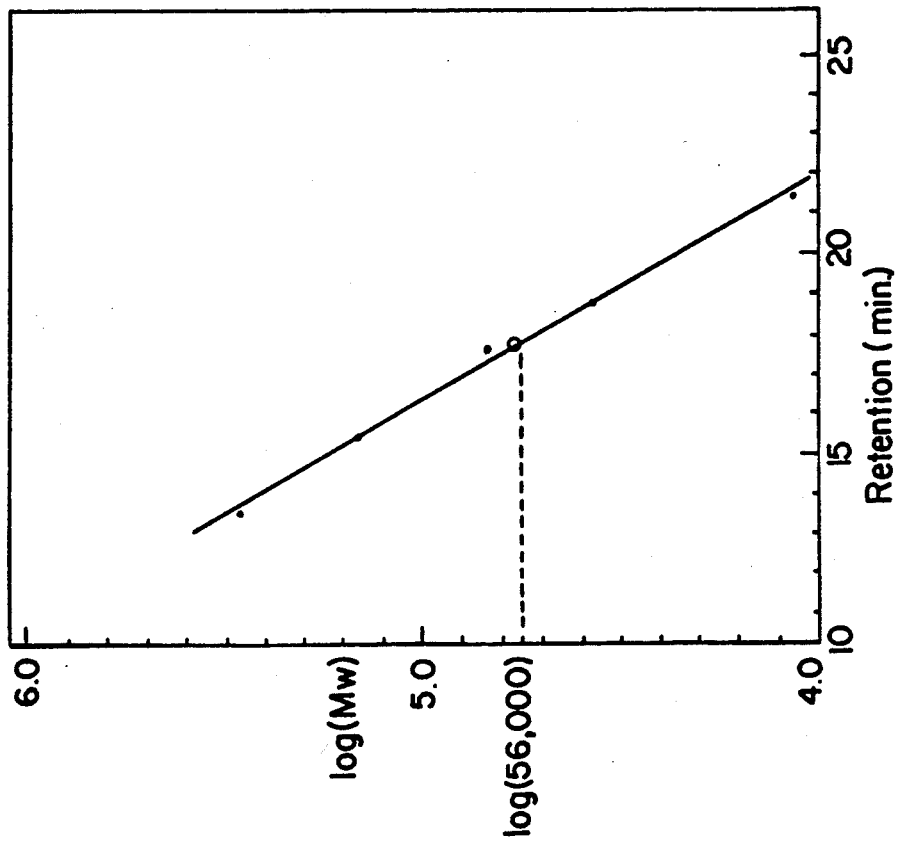
FIG. 25 shows the result of the determination of the molecular weight of the protease specific for a basic amino acid residue of the present invention by gel filtration with the use of TSK gel G3000 $SW_{XL}$.
Figure 24:
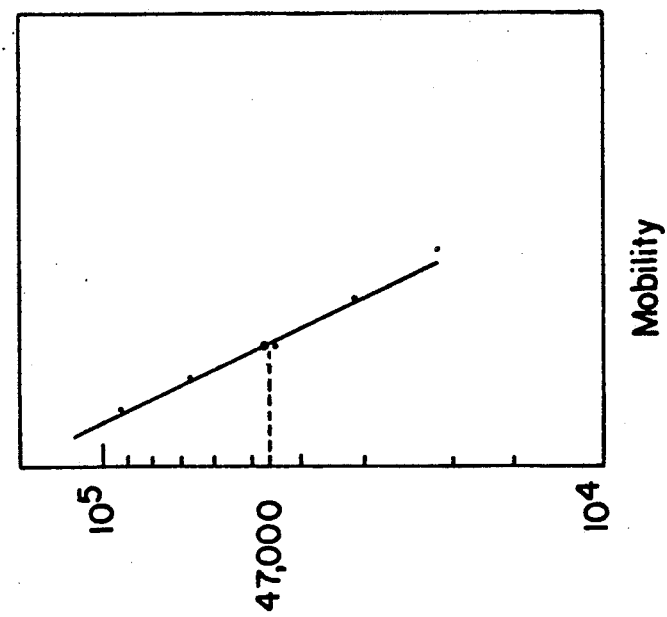
FIG. 24 shows the result of the determination of the molecular weight of the protease specific for a basic amino acid residue of the present invention by electrophoresis with the use of 7.5% gel.

Isoelectric point and molecular weight of protease specific for basic amino acid residue The apparent molecular weight of the enzyme was approximately 47,000 when determined by SDS-PAGE with the use of a 12.5% gel (cf. FIG. 24) and approximately 56,000 when determined by gel filtration with the use of TSK gel G3000 $SW_{XL}$, however without use of Lubrol PX (cf. FIG. 25).

The isoelectric point (pI) of this enzyme determined by isoelectric electrophoresis with the use of IEF gel 3-9 was 4.5 (cf. FIG. 26).

The invention claimed is:

1. A protease having enzymatic properties with respect to (a) function and substrate specificity, (b) optimum pH, (f) activation, and (g) inhibition, as follows:
   (a) said protease hydrolyzes a peptide bond on the C-terminal side of Y of a peptide X—Y—, wherein X is Arg, Lys or Pro and has a peptide bond on the N-terminal side thereof, Y is Arg, and the hyphens each indicate a peptide bond;
(b) said protease has an optimum pH of about 7.0 in Tris-hydrochloride buffer;
(f) said protease is activated with calcium chloride or a surfactant; and
(g) said protease is inhibited with p-amidinophenylmethanesulfonyl fluoride, p-chloromercuribenzoic acid, a metal chelater, tetraacetic acid or a heavy metal.

2. A protease as claimed in claim 1, wherein said protease is obtained from a culture broth in which a yeast has been cultured, said yeast belonging to the genus Sporobolomyces.

3. A protease as claimed in claim 1, wherein said protease has enzymatic properties with respect to (c) pH stability, (d) optimum temperature and (e) heat stability as follows:
(c) said protease is most stable at a pH of from 6.0 to 8.0;
(d) said protease has an optimum temperature of about 40° to 47° C. at pH 7.0; and
(e) said protease is stable up to 38° C. at a pH of 7.0 for 10 minutes.

4. A protease having enzymatic properties with respect to (a) function and substrate specificity, (f) activation, and (g) inhibition, as follows:
(a) said protease hydrolyzes a peptide bond on the C-terminal side of Y of a peptide X—Y—, wherein X is Arg, Lys or Pro and has a peptide bond on the N-terminal side thereof, Y is Arg, and the hyphens each indicate a peptide bond;
(f) said protease is activated with calcium chloride or a surfactant; and
(g) said protease is inhibited with p-amidinophenylmethanesulfonyl fluoride, p-chloromercuribenzoic acid, a metal chelater, tetraacetic acid or a heavy metal.

5. A protease having enzymatic properties with respect to (a) function and substrate specificity, (b) optimum pH, (f) activation, and (g) inhibition, as follows:
(a) said protease hydrolyzes a peptide bond on the C-terminal side of Y of a peptide X—Y—, wherein X is Arg, Lys or Pro, Y is Arg, and the hyphens each indicate a peptide bond;
(b) said protease has an optimum pH of about 7.0 in Tris-hydrochloride buffer;
(f) said protease is activated with calcium chloride or a surfactant; and
(g) said protease is inhibited with p-amidinophenylmethanesulfonyl fluoride, p-chloromecuribenzoic acid, a metal chelater, tetraacetic acid or a heavy metal.

6. A protease as claimed in claim 5, wherein said protease is obtained from a culture broth in which a yeast has been cultured, said yeast belonging to the genus Sporobolomyces.

7. A protease as claimed in claim 1, wherein said protease has enzymatic properties with respect to (c) pH stability, (d) optimum temperature and (e) heat stability as follows:
(c) said protease is most stable at a pH of from 6.0 to 10;
(d) said protease has an optimum temperature of about 60° C. at a pH of 7.0; and
(e) said protease is stable up to 55° C. at a pH of 7.0 for 10 minutes.

8. A protease as claimed in claim 5, wherein said protease has enzymatic properties with respect to (c) pH stability, (d) optimum temperature and (e) heat stability as follows:
(c) said protease is most stable at a pH of from 6.0 to 8.0;
(d) said protease has an optimum temperature of about 40° to 47° C. at a pH of 7.0; and
(e) said protease is stable up to 38° C. at a pH of 7.0 for 10 minutes.

9. A protease as claimed in claim 5, wherein said protease has enzymatic properties with respect to (c) pH stability, (d) optimum temperature and (e) heat stability as follows:
(c) said protease is most stable at a pH of from 6.0 to 10;
(d) said protease has an optimum temperature of about 60° C. at a pH or 7.0; and
(e) said protease is stable up to 55° C. at a pH of 7.0 for 10 minutes.

10. A protease as claimed in claim 1, wherein said protease is obtained from a culture broth in which a yeast has been cultured, said yeast belonging to a genus selected from the group consisting of Kluyveromyces, Filobasidium, Hansenula, Issatchenkia, Pichia, Rhodosporidium and Saccharomycopsis.

11. A protease as claimed in claim 5, wherein said protease is obtained from a culture broth in which a yeast has been cultured, said yeast belonging to a genus selected from the group consisting of Kluyveromyces, Filobasidium, Hansenula, Issatchenkia, Pichia, Rhodosporidium and Saccharomycopsis.

12. A protease as claimed in claim 4, wherein said protease is obtained from a culture broth in which a yeast has been cultured, said yeast belonging to the genus Sporobolomyces.

13. A protease as claimed in claim 4, wherein said protease is obtained from a culture broth in which a yeast has been cultured, said yeast belonging to a genus selected from the group consisting of Kluyveromyces, Filobasidium, Hansenula, Issatchenkia, Pichia, Rhodosporidium and Saccharomycopsis.

14. A protease as claimed in claim 3, wherein said protease is obtained from a culture broth in which a yeast has been cultured, said yeast belonging to the genus Sporobolomyces.

15. A protease as claimed in claim 8, wherein said protease is obtained from a culture broth in which a yeast has been cultured, said yeast belonging to the genus Sporobolomyces.

16. A protease as claimed in claim 7, wherein said protease is obtained from a culture broth in which a yeast has been cultured, said yeast belonging to a genus selected from the group consisting of Kluyveromyces, Filobasidium, Hansenula, Issatchenkia, Pichia, Rhodosporidium and Saccharomycopsis.

17. A protease as claimed in claim 9, wherein said protease is obtained from a culture broth in which a yeast has been cultured, said yeast belonging to a genus selected from the group consisting of Kluyveromyces, Filobasidium, Hansenula, Issatchenkia, Pichia, Rhodosporidium and Saccharomycopsis.

18. A protease as claimed in claim 3, wherein said protease has a molecular weight of about 47,000 as determined by gel filtration and an isoelectric point of 4.5 as determined by isoelectric electrophoresis.

19. A protease as claimed in claim 8, wherein said protease has a molecular weight of about 47,000 as determined by gel filtration and an isoelectric point of 4.5 as determined by isoelectric electrophoresis.

20. A protease as claimed in claim 7, wherein said protease has a molecular weight of about 100,000 as determined by gel filtration.

21. A protease as claimed in claim 9, wherein said protease has a molecular weight of about 100,000 as determined by gel filtration.

22. A protease as claimed in claim 2, wherein said protease is obtained from a culture broth in which a yeast has been cultured, said yeast being the strain *Sporobolomyces odrus* IFO 1597.

23. A protease as claimed in claim 6, wherein said protease is obtained from a culture broth in which a yeast has been cultured, said yeast being the strain *Sporobolomyces odrus* IFO 1597.

24. A protease as claimed in claim 12, wherein said protease is obtained from a culture broth in which a yeast has been cultured, said yeast being the strain *Sporobolomyces odrus* IFO 1597.

25. A protease as claimed in claim 10, wherein said protease is obtained from a culture broth in which a yeast has been cultured, said yeast being selected from the group of strains consisting of *Kluyveromyces lactis* IFO 1903, *K. lactis* IFO 1267, *Filobasidium capsuligenum* IFO 1119, *F. capsuligenum* IFO 1185, *Hansenula fabianii* IFO 1253, *H. fabianii* IFO 1254, *Hansenula holstii* IFO 0980, *H. holstii* IFO 0986, *Hansenula polymorpha* ATTC 20612, *Issatchenkia scutulata* IFO 10069, *I. scutulata* IFO 10070, *Pichia heedii* IFO 10019, *P. heedii* 10020, *Pichia heedi* var. thermotolerans IFO 10024, *P. heedii* var. thermotolerans IFO 10025, *P. heedii* var. thermotolerans IFO 10026, *Rhodosporidium diovoatum* IFO 1830, *Rhodosporidium toruloides* IFO 0413, *R. toruloides* IFO 0080, *Saccaromycopsis fibuligera* IFO 0103, *S. fibuligera* IFO 0105 and *S. fibuligera* IFO 0106.

26. A protease as claimed in claim 11, wherein said protease is obtained from a culture broth in which a yeast has been cultured, said yeast being selected from the group of strains consisting of *Kluyveromyces lactis* IFO 1903, *K. lactis* IFO 1267, *Filobasidium capsuligenum* IFO 1119, *F. capsuligenum* IFO 1185, *Hansenula fabianii* IFO 1253, *H. fabianii* IFO 1254, *Hansenula holstii* IFO 0980, *H. holstii* IFO 0986, *Hansenula polymorpha* ATTC 20612, *Issatchenkia scutulata* IFO 10069, *I. scutulata* IFO 10070, *Pichia heedii* IFO 10019, *P. heedii* 10020, *Pichia heedi* var. thermotolerans IFO 10024, *P. heedii* var. thermotolerans IFO 10025, *P. heedii* var. thermotolerans IFO 10026, *Rhodosporidium diovoatum* IFO 1830, *Rhodosporidium toruloides* IFO 0413, *R. toruloides* IFO 0080, *Saccaromycopsis fibuligera* IFO 0103, *S. fibuligera* IFO 0105 and *S. fibuligera* IFO 0106.

27. A protease as claimed in claim 13, wherein said protease is obtained from a culture broth in which a yeast has been cultured, said yeast being selected from the group of strains consisting of *Kluyveromyces lactis* IFO 1903, *K. lactis* IFO 1267, *Filobasidium capsuligenum* IFO 1119, *F. capsuligenum* IFO 1185, *Hansenula fabianii* IFO 1253, *H. fabianii* IFO 1254, *Hansenula holstii* IFO 0980, *H. holstii* IFO 0986, *Hansenula polymorpha* ATTC 20612, *Issatchenkia scutulata* IFO 10069, *I. scutulata* IFO 10070, *Pichia heedii* IFO 10019, *P. heedii* 10020, *Pichia heedi* var. thermotolerans IFO 10024, *P. heedii* var. thermotolerans IFO 10025, *P. heedii* var. thermotolerans IFO 10026, *Rhodosporidium diovoatum* IFO 1830, *Rhodosporidium toruloides* IFO 0413, *R. toruloides* IFO 0080, *Saccaromycopsis fibuligera* IFO 0103, *S. fibuligera* IFO 0105 and *S. fibuligera* IFO 0106.

28. A protease having enzymatic properties with respect to (a) function and substrate specificity, (f) activation, and (g) inhibition, as follows:
  (a) said protease hydrolyzes a peptide bond on the C-terminal side of Y of a peptide X—Y—, wherein X is Arg, Lys, or Pro, Y is Arg, and the hyphens each indicate a peptide bond;
  (f) said protease is activated with calcium chloride or a surfactant; and
  (g) said protease is inhibited with p-amidinophenyl-methanesulfonyl fluoride, p-chloromercuribenzoic acid, a metal chelater, tetraacetic acid or a heavy metal.

29. A protease as claimed in claim 28, wherein said protease is obtained from a culture broth in which a yeast has been cultured, said yeast belonging to the genus Sporobolomyces.

30. A protease as claimed in claim 28, wherein said protease is obtained from a culture broth in which a yeast has been cultured, said yeast belonging to a genus selected from the group consisting of Kluyveromyces, Filobasidium, Hansenula, Issatchenkia, Pichia, Rhodosporidium and Saccharomycopsis.

31. A protease as claimed in claim 4, wherein said protease has a molecular weight of about 47,000 as determined by gel filtration and an isoelectric point of 4.5 as determined by isoelectric electrophoresis.

32. A protease as claimed in claim 4, wherein said protease has a molecular weight of about 100,000 as determined by gel filtration.

33. A protease as claimed in claim 28, wherein said protease has a molecular weight of about 47,000 as determined by gel filtration and an isoelectric point of 4.5 as determined by isoelectric electrophoresis.

34. A protease as claimed in claim 28, wherein said protease has a molecular weight of about 100,000 as determined by gel filtration.

35. A protease as claimed in claim 29, wherein said protease is obtained from a culture broth in which a yeast has been cultured, said yeast being the strain *Sporobolomyces odrus* IFO 1597.

36. A protease as claimed in claim 30, wherein said protease is obtained from a culture broth in which a yeast has been cultured, said yeast being selected from the group of strains consisting of *Kluyveromyces lactis* IFO 1903, *K. lactis* IFO 1267, *Filobasidium capsuligenum* IFO 1119, *F. capsuligenum* IFO 1185, *Hansenula fabianii* IFO 1253, *H. fabianii* IFO 1254, *Hansenula holstii* IFO 0980, *H. holstii* IFO 0986, *Hansenula polymorpha* ATTC 20612, *Issatchenkia scutulata* IFO 10069, *I. scutulata* IFO 10070, *Pichia heedii* IFO 10019, *P. heedii* 10020, *Pichia heedi* var. thermotolerans IFO 10024, *P. heedii* var. thermotolerans IFO 10025, *P. heedii* var. thermotolerans IFO 10026, *Rhodosporidium diovoatum* IFO 1830, *Rhodosporidium toruloides* IFO 0413, *R. toruloides* IFO 0080, *Saccaromycopsis fibuligera* IFO 0103, *S. fibuligera* IFO 0105 and *S. fibuligera* IFO 0106.

* * * * *